(12) United States Patent
Gellman et al.

(10) Patent No.: US 7,304,165 B2
(45) Date of Patent: *Dec. 4, 2007

(54) OLIGOMERS AND POLYMERS OF DI-SUBSTITUTED CYCLIC IMINO CARBOXYLIC ACIDS

(75) Inventors: Samuel H. Gellman, Madison, WI (US); Bayard R. Huck, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 495 days.

This patent is subject to a terminal disclaimer.

(21) Appl. No.: 10/761,556

(22) Filed: Jan. 21, 2004

(65) Prior Publication Data

US 2004/0152133 A1   Aug. 5, 2004

Related U.S. Application Data

(60) Division of application No. 09/883,579, filed on Jun. 18, 2001, now Pat. No. 6,710,186, which is a continuation-in-part of application No. 09/592,756, filed on Jun. 13, 2000, now Pat. No. 6,727,368.

(60) Provisional application No. 60/138,972, filed on Jun. 14, 1999.

(51) Int. Cl.
   *C07D 295/00*   (2006.01)
(52) U.S. Cl. ........................ 548/538; 548/518; 548/530
(58) Field of Classification Search .................... None
   See application file for complete search history.

(56) References Cited

U.S. PATENT DOCUMENTS 6,710,186 B2 * 3/2004 Gellman et al. ............ 548/538

OTHER PUBLICATIONS

Parsons, J. A. Peptide Hormones. Baltimore: University Park Press. 1976, pp. 1-6.*

* cited by examiner

*Primary Examiner*—Jon Epperson
(74) *Attorney, Agent, or Firm*—Joseph T. Leone, Esq.; DeWitt Ross & Stevens S.C.

(57) ABSTRACT

Disclosed are cyclic imino oligomers and polymers comprised of subunits of the formula:

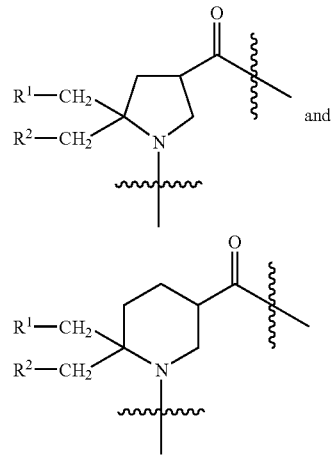

Also disclosed are combinatorial libraries and arrays of the cyclic imino compounds.

15 Claims, 10 Drawing Sheets observed NOEs

OLIGOMERS AND POLYMERS OF DI-SUBSTITUTED CYCLIC IMINO CARBOXYLIC ACIDS

CROSS REFERENCE TO RELATED APPLICATIONS

This is a divisional of application Ser. No. 09/883,579, filed Jun. 18, 2001 (now U.S. Pat. No. 6,710,186, issued Mar. 24, 2004), which is a continuation-in-part of application Ser. No. 09/592,756, filed Jun. 13, 2000 (now U.S. Pat. No. 6,727,368, issued Apr. 27, 2004), which claims priority to provisional application Ser. No. 60/138,972, filed Jun. 14, 1999, the entire contents of all of which are incorporated herein by reference.

FIELD OF THE INVENTION

The present invention is directed to unnatural polypeptide-like molecules which are oligomers or polymers of constrained, di-substituted imino carboxylic acids, methods of generating combinatorial libraries using these residues, and combinatorial libraries formed thereby.

DESCRIPTION OF THE PRIOR ART

Chemists have long sought to extrapolate the power of biological catalysis and recognition to synthetic systems. These efforts have focused largely on low molecular weight catalysts and receptors. Most biological systems, however, rely almost exclusively on large polymers such as proteins and RNA to perform complex chemical functions.

Proteins and RNA are unique in their ability to adopt compact, well-ordered conformations. These two biopolymers are unique also because they can perform complex chemical operations (e.g., catalysis, highly selective recognition, etc.). Folding is linked to function in both proteins and RNA because the creation of an "active site" requires proper positioning of reactive groups. Consequently, there has been a long-felt need to identify synthetic polymer backbones which display discrete and predictable folding propensities (hereinafter referred to as "foldamers") to mimic natural biological systems. Such backbones will provide molecular "tools" to probe the functionality of large-molecule interactions (e.g. protein-protein and protein-RNA interactions).

Much work on β-amino acids and peptides synthesized therefrom has been performed by a group led by Dieter Seebach in Zurich, Switzerland. See, for example, Seebach et al. (1996) *Helv. Chim. Acta*. 79:913-941; and Seebach et al. (1996) *Helv. Chim. Acta*. 79:2043-2066. In the first of these two papers Seebach et al. describe the synthesis and characterization of a β-hexapeptide, namely (H-β-HVal-β-HAla-β-HLeu)$_2$-OH. Interestingly, this paper specifically notes that prior art reports on the structure of β-peptides have been contradictory and "partially controversial." In the second paper, Seebach et al. explore the secondary structure of the above-noted β-hexapeptide and the effects of residue variation on the secondary structure.

Dado and Gellman (1994) *J. Am. Chem. Soc.* 116:1054-1062 describe intramolecular hydrogen bonding in derivatives of β-alanine and γ-amino butyric acid. This paper postulates that β-peptides will fold in manners similar to α-amino acid polymers if intramolecular hydrogen bonding between nearest neighbor amide groups on the polymer backbone is not favored.

Suhara et al. (1996) *Tetrahedron Lett.* 37(10):1575-1578 report a polysaccharide analog of a β-peptide in which D-glycocylamine derivatives are linked to each other via a C-1 β-carboxylate and a C-2 α-amino group. This class of compounds has been given the trivial name "carbopeptoids."

Regarding methods to generate combinatorial libraries, several recent reviews are available. See, for instance, Ellman (1996) *Acc. Chem. Res.* 29:132-143 and Lam et al. (1997) *Chem. Rev.* 97:411-448.

SUMMARY OF THE INVENTION

The present invention is drawn to a genus of oligomers and polymers of conformationally-restricted, di-substituted imino carboxylic acids. The preferred oligomers and polymers of the invention strongly favor a discrete secondary structure (although this is not a requirement of the invention). These stable secondary structures include helices analogous to the well-known poly(proline) II helical structure seen in α-amino acids.

More specifically, the invention is directed to compounds comprising formula:

X—{A}$_n$—Y wherein n is an integer greater than 1; and
each A, independent of every other A, is selected from the group consisting of:

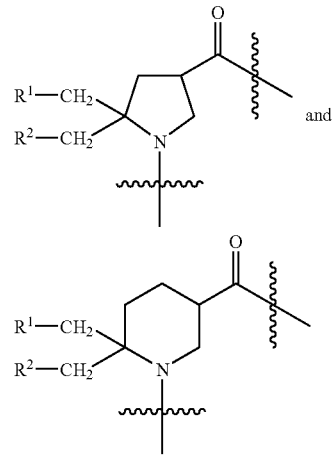

wherein $R^1$ and $R^2$ are independently selected from the group consisting of hydrogen, hydroxy, linear or branched $C_1$-$C_{16}$-alkyl, alkenyl, or alkynyl; mono- or di-$C_1$-$C_{16}$ alkylamino; mono- or bicyclic aryl; mono- or bicyclic heteroaryl having up to 5 heteroatoms selected from N, O, and S; mono- or bicyclic aryl-$C_1$-$C_{16}$-alkyl; mono- or bicyclic heteroaryl-$C_1$-$C_{16}$-alkyl; —(CH$_2$)$_{0-6}$—OR$^3$, —(CH$_2$)$_{0-6}$—SR$^3$, —(CH$_2$)$_{0-6}$—S(=O)—CH$_2$—R$^3$, —(CH$_2$)$_{0-6}$—S(=O)$_2$—CH$_2$—R$^3$, —(CH$_2$)$_{0-6}$—NR$^3$R$^3$, —(CH$_2$)$_{0-6}$—NHC(=O)R$^3$, —(CH$_2$)$_{0-6}$—NHS(=O)$_2$—CH$_2$—R$^3$, —(CH$_2$)$_{0-6}$—O—(CH$_2$)$_{2-6}$—R$^4$, —(CH$_2$)$_{0-6}$—S—(CH$_2$)$_{2-6}$—R$^4$, —(CH$_2$)$_{0-6}$—S(=O)—(CH$_2$)$_{2-6}$—R$^4$, —(CH$_2$)$_{0-6}$—S(=O)$_2$—(CH$_2$)$_{2-6}$—R$^4$, —(CH$_2$)$_{0-6}$—NH—(CH$_2$)$_{2-6}$—R$^4$, —(CH$_2$)$_{0-6}$—N—{(CH$_2$)$_{2-6}$—R$^4$}$_2$, —(CH$_2$)$_{0-6}$—NHC(=O)—(CH$_2$)$_{2-6}$—R$^4$, and —(CH$_2$)$_{0-6}$—NHS(=O)$_2$—(CH$_2$)$_{2-6}$—R$^4$; wherein $R^3$ is independently selected from the group consisting of hydrogen, $C_1$-$C_6$-alkyl, alkenyl, or alkynyl; mono-or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and $R^4$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane;

one of X or Y is hydrogen or an amino-terminal capping group;

the other of X or Y is hydroxy or a carboxy-terminal capping group;

and salts thereof.

As noted above, each "A" substituent is selected independently from one another. Consequently, the invention explicitly encompasses both homo-oligomers and polymers, as well as hetero-oligomers and polymers.

Encompassed within the invention are protected forms of the above compounds in which reactive carboxy and amino subtituents are protected by selectively removable (including orthogonally removable) moieties. All substituents used as protecting groups in synthetic organic chemistry are encompassed within the definition. For purposes of this application, a "protecting group" is a chemical moiety capable of selective addition to and removal from a reactive site to allow manipulation of a chemical entity at sites other than the reactive site. A host of protecting groups are known in the art. An illustrative, non-limiting list of protecting groups includes methyl, formyl, ethyl, acetyl, t-butyl, anisyl, benzyl, trifluoroacetyl, N-hydroxysuccinimide, t-butoxycarbonyl, benzoyl, 4-methylbenzyl, thioanisolyl, thiocresyl, benzyloxymethyl, 4-nitrophenyl, benzyloxycarbonyl, 2-nitrobenzoyl, 2-nitrophenylsulphenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, and 2,2,5,7,8-pentamethyl-chroman-6-sulfonyl. Expressly included within this definition, without limitation, are carbamate-forming protecting groups such as Boc, Fmoc, Cbz, and the like, and amide-forming protecting groups such as acetyl and the like. Such protecting groups are well known and widely used by those skilled in the art of peptide chemistry.

All stereochemical configurations (single enantiomers, single diastereomers, mixtures thereof, and racemates thereof) of the compounds described above are encompassed within the scope of the invention. In the preferred embodiment, all of the residues share the same absolute configuration (either R or S) about the asymmetric ring carbon in the position α to the exocyclic carbonyl carbon.

The invention is further directed to a method for preparing a combinatorial library of the subject compounds, the method comprising at least two successive iterations of first covalently linking a first {A} subunit via its C terminus to a plurality of separable solid substrates, the first subunit selected from the group recited above for "A," and then randomly dividing the plurality of substrates into at least two sub-groups and deprotecting the first subunits attached to the at least two sub-groups. Then in separate and independent reactions, covalently linking to the first subunit of each of the at least two sub-groups a second subunit independently selected from the above-listed group of {A} residues.

The invention is further drawn to a combinatorial library of oligomers and/or polymers comprising a plurality of different compounds as described above, each compound covalently linked to a solid support, the combinatorial library produced by the process described immediately above.

Another embodiment of the invention is drawn to an array comprising a plurality of compounds as described above at selected, known locations on a substrate or in discrete solutions, wherein each of the compounds is substantially pure within each of the selected known locations and has a composition which is different from other polypeptides disposed at other selected and known locations on the substrate.

The primary advantage and utility of the present invention is that it allows the construction of synthetic peptides having high conformational stability. These synthetic polyamides have practical utility in investigating the biological interactions involving biopolymers, by, for example, constructing support-bound libraries of the compounds and exposing putative pharmacologically active agents to the support-bound compounds. Thus, the compounds and libraries of the compounds can be used to screen other potentially active compounds.

The stable secondary structure of the present compounds also allows them to mimic natural protein secondary structure, thereby allowing targeted disruption of large-molecule interactions (e.g., protein-protein interactions.) In this instance, the compounds have utility as models of naturally-occuring alpha polypeptides. However, because the present compounds lack alpha peptide linkages, they are less prone to degradation by proteolytic enzymes.

It is also expected that the compounds of the present invention will readily cross biological membranes due to their lower polarity as compared to natural peptides. This is expected based upon the known ability of proline oligomers to cross biological membranes. Because the backbone of the subject oligomers and polymers is linked by tertiary amide bonds, the compounds lack acidic amide protons on the backbone. Additionally, because the compounds are unnatural, they are expected to resist enzymatic cleavage (as noted above). Therefore, the subject oligomers have utility as probes to investigate the ability of non-natural betapeptides to cross biological membranes.

As a natural consequence, the invention is further drawn to the use of these synthetic polyamides as base molecules from which to synthesize large libraries of novel compounds utilizing the techniques of combinatorial chemistry. In addition to varying the primary sequence of the residues, the ring positions of these compounds can be substituted with a wide variety of substituents, such as those described above for $R^1$ and $R^2$. The main advantage here is that substituents placed on the backbone rings do not interfere with the ability of the compounds to adopt a regular secondary structure. Consequently, the subject compounds can be utilized to construct vast libraries having different substituents, but all of which share a stabilized secondary structure. This utility is highly desirable because, as a general principal, chemical structure is responsible for chemical activity. By providing a means for constructing large libraries or arrays of the subject compounds, their structure-activity relationships can be cogently investigated by rational design of libraries or arrays containing systematically altered permutations of the oligomers disclosed herein.

Other aims, objects, and advantages of the invention will appear more fully from a complete reading of the following Detailed Description of the Invention and the attached claims.

DETAILED DESCRIPTION OF THE INVENTION

Figure 1:
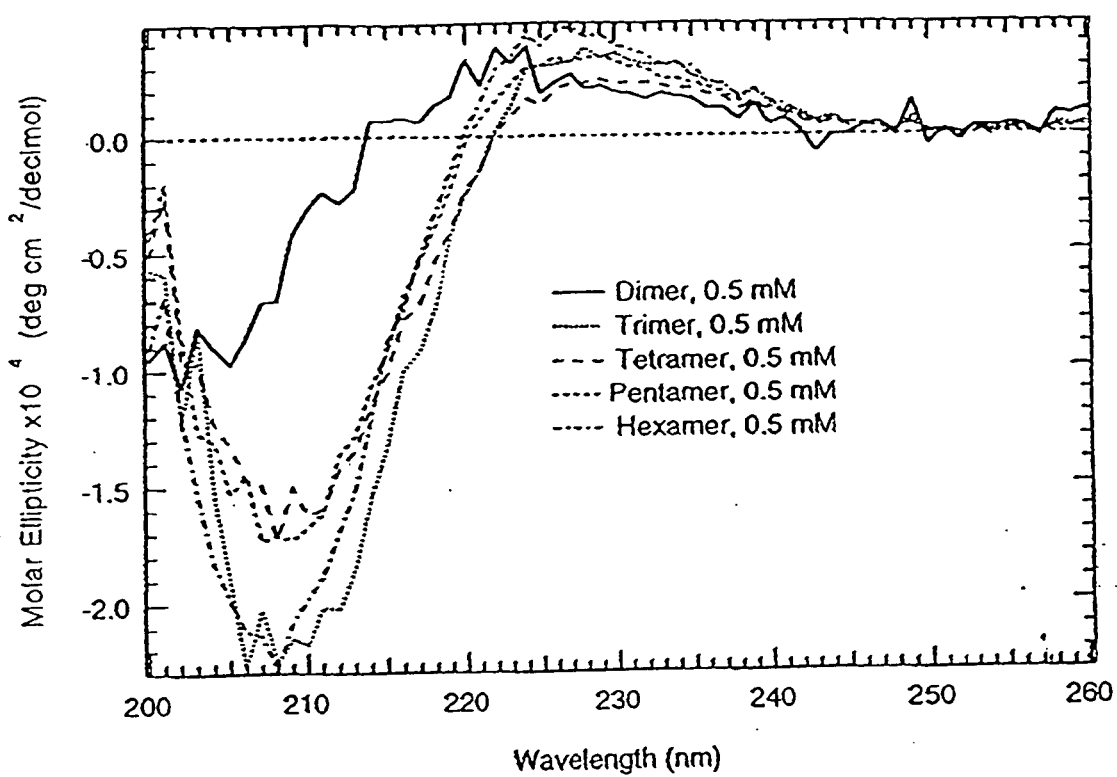
FIG. 1 depicts the CD spectra (in methanol) of nipecotic acid oligomers from the dimer to the hexamer.

Abbreviations and Definitions:

The following abbreviations are used throughout the specification and claims. Unless specifically defined to the contrary, all other terms have their standard accepted meanings. All of the following compounds can be purchased commercially from Aldrich Chemical Company, Milwaukee, Wis., USA, as well as other national and international suppliers:

"alkyl"=$C_1$-$C_6$ straight or branched alkyl
"Bn"=benzyl
"BnBr"=benzyl bromide
"Boc"=tert-butoxycarbonyl
"BopCl"=bis(2-oxo-3-oxazolidinyl)phosphinic chloride
"cis-5-MOM-PCA"=cis-5 methoxymethyl-3-pyrrolidine carboxylic acid
"Cbz"=carbobenzyloxy
"CSA"=10-camphorsulfonic acid
"DIEA"=diisopropyl ethyl amine
"DMAP"=N,N-dimethylaminopyridine
"DMF"=N,N-dimethylformamide
"EDCI"=N,N-dimethylaminopropyl-3-ethylcarbodiimide "FAB MS"=fast atom bombardment mass spectrometry
"Iso-Cl"=isobutyryl chloride
"MALDI-TOF MS"=matrix-assisted laser desorption ionization, time-of-flight mass spectrometry
"Nip"=nipecotic acid
"PCA"=pyrrolidine carboxylic acid
"PiCA"=piperazine carboxylic acid
"TBAF"=tetrabutylammonium fluoride
"TCMP"=trans-3-carboxy-4-methylpiperidine
"THF"=tetrahydrofuran
"TMSCHN$_2$"=(trimethylsilyl)diazomethane
"Ts-Cl"=p-toluenesulfonyl chloride Chemistry:

General. Melting points are uncorrected. $CH_2Cl_2$ was freshly distilled from $CaH_2$ under $N_2$. DMF was distilled under reduced pressure from ninhydrin and stored over 4 Å molecular sieves. Triethylamine was distilled from $CaH_2$ before use. Other solvents and reagents were used as obtained from commercial suppliers. For BOC removal, 4 M HCl in dioxane from was used. Column chromatography was carried out by using low air pressure (typically 6 psi) with 230-400 mesh silica gel 60. Routine $^1H$-NMR spectra were obtained on a Bruker AC-300 and are referenced to residual protonated NMR solvent. Routine $^{13}C$-NMR spectra were obtained on a Bruker AC-300 and are referenced to the NMR solvent. High resolution electron impact mass spectroscopy was performed on a Kratos MS-80RFA spectrometer with DS55/DS90.

Far UV Circular Dichroism (CD). Data were obtained on a Jasco J-715 instrument at 20° C. In all CD plots contained herein, the mean residue ellipticity is presented on the vertical axis. Presenting the mean residue ellipticity is a standard practice in peptide chemistry wherein the intensity of each CD spectrum is normalized for the number of amide chromophores in the peptide backbone. Consequently, when the intensity of the minimum (ca. 208 nm) peak characteristic of secondary structure formation increases with increasing chain length, this change represents an increase in the population of the secondary structure, rather than simply an increase in the number of chromophores present in each molecule.

General Experimental Procedure A. Peptide Couplings Using Bop-Cl as the Coupling Reagent. Boc-Xxx-OBn (1.0 eq.) was dissolved in 4 N HCl/dioxane (2.5 eq.). The solution was stirred for 2 h, the solvent was removed under a stream of $N_2$, and the residue was dried under vacuum to give a white solid (Xxx-OBn.HCl). This material was dissolved in methylene chloride (0.1 M). Boc-Xxx-OH (1.0 eq.) was added and the reaction mixture was cooled to 0° C. BopCl (1.0 eq.) was added, followed by DIEA (2.0 eq.). The reaction mixture was stirred for 48 h at 5° C. in the cold room. The reaction mixture was removed from the cold room and poured into a solution of diethyl ether (3× reaction volume) and $H_2O$ (2× reaction volume). The organic layer was isolated and washed with saturated $KHSO_4$, saturated $NaHCO_3$, and brine. The organic layer was dried over $MgSO_4$ and concentrated. The crude product was then purified by column chromatography to give Boc-(Xxx)$_2$-OBn.

General Experimental Procedure B. Peptide Couplings Using Bop-Cl as the Coupling Reagent. Boc-Xxx-OBn (1.0 eq.) was dissolved in 4 N HCl/dioxane (2.5 eq.). The solution was stirred for 2 h, the solvent was removed under a stream of $N_2$, and the residue was dried under vacuum to give a white solid (Xxx-OBn.HCl). This material was dissolved in methylene chloride (0.2 M). Boc-Xxx-OH (1.0 eq.) was added and the reaction mixture was cooled to 0° C. BopCl (1.0 eq.) was added, followed by DIEA (2.5 eq.). The reaction mixture was stirred for 48 h at room temperature. The reaction mixture was poured into a solution of diethyl ether (3× reaction volume) and $H_2O$ (2× reaction volume). The organic layer was isolated and washed with saturated $KHSO_4$, saturated $NaHCO_3$, and brine. The organic layer was dried over $MgSO_4$ and concentrated. The crude product was then purified by column chromatography to give Boc-$(Xxx)_2$-OBn.

Nipecotic Acid Oligomers

1. Synthesis of the Protected Monomer

Boc-(S)-Nip-OBn or Boc-(R)-Nip-OBn is the building block for the synthesis of nipecotic acid oligomers. The protected monomer was synthesized in three steps beginning with a resolution via co-crystallization with (+) or (−) CSA. The amino group was then protected as the tert-butyl carbamate, and the carboxyl group was protected as the benzyl ester.

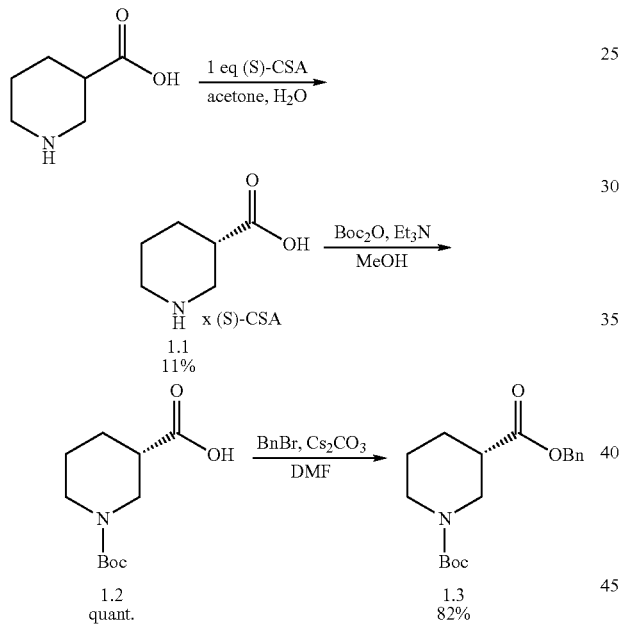

(S)-Nip.(S)-CSA 1.1. (1S)-(+)-10-Camphorsulfonic acid (11.62 g, 0.05 mol) was added to a stirred solution of racemic nipecotic acid (6.46 g, 0.05 mol) in acetone (100 mL). The solution was heated to reflux, and $H_2O$ (15 mL) was added until all solids dissolved. The solution was cooled to room temperature and allowed to stir overnight. The precipitate that formed was isolated by filtration and recrystallized three times with acetone/$H_2O$ (6/1, v/v) to afford 1.99 g (11% yield) of the desired product as a white solid: m.p. 221-223° C.; $\{a\}_D$+25.3° (c 1.0, MeOH).

Boc-(S)-Nip-OH 1.2. (S)-Nip.(S)-CSA (1.90 g, 5.3 mmol) was dissolved in methanol (12 mL). Triethylamine (2.2 mL, 15.8 mmol) and di-tert-butyl dicarbonate (1.38 g, 6.3 mmol) were added and the solution was stirred at 50° C. for 12 h. The solution was then concentrated, and the residue was dissolved in $H_2O$. The aqueous solution was washed with diethyl ether, and the organic layer was discarded. The aqueous layer was acidified to pH 3 with 1 M HCl and extracted with $CH_2Cl_2$. The organic layer was dried over $MgSO_4$ and concentrated to afford 1.24 g (quantitative yield) of the desired product as a white solid: m.p. 166-168° C.; FAB-MS m/z (M+Na$^+$) calcd for $C_{11}H_{19}NO_4Na$ 252.3, obsd 252.5.

Boc-(S)-Nip-OBn 1.3. Boc-(S)-Nip-OH (0.70 g, 3.1 mmol) was dissolved in N,N-dimethylformamide (DMF) (14 mL). $Cs_2CO_3$ (1.0 g, 3.1 mmol) and benzyl bromide (0.41 mL, 3.5 mmol) were added, and the solution was stirred at room temperature for 24 h. The solution was then concentrated, and the residue was dissolved in $H_2O$. The aqueous solution was then extracted with $CH_2Cl_2$. The organic solution was dried over $MgSO_4$ and concentrated to give an oil. The crude product was purified by column chromatography eluting with ethyl acetate/hexanes (1/3, v/v) to afford 0.81 g (82% yield) of the desired product as a white solid.

2. Oligomer Synthesis

Oligomers of nipecotic acid were synthesized in a stepwise fashion using standard coupling procedures:

The reaction scheme is as follows:

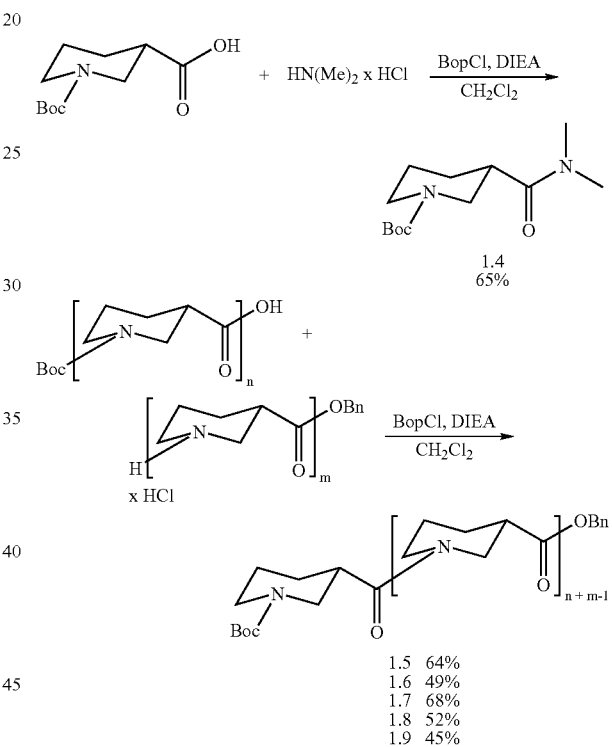

1.5 64%
1.6 49%
1.7 68%
1.8 52%
1.9 45%

Boc-(S)-Nip-N(Me)$_2$ 1.4. Via general procedure A, HCl.N(Me)$_2$ (0.29 g, 3.5 mmol) was coupled with Boc-(S)-Nip-OH (0.4 g, 1.7 mmol). After workup, the crude product was purified by column chromatography eluting with ethyl acetate/hexanes (1/1, v/v) to afford 0.29 g (65% yield) of the desired product as a colorless oil; FAB-MS m/z (M+Na$^+$) calcd for $C_{11}H_{19}NO_4Na^+$ 279.3, obsd 279.1.

Boc-{(S)-Nip}$_2$-OBn 1.5. Via general procedure A, Boc (S)-Nip-OBn (0.80 g, 2.5 mmol) was Boc-deprotected and coupled with Boc-(S)-Nip-OH (0.64 g, 2.5 mmol). After workup, the crude product was purified by column chromatography eluting with ethyl acetate/hexanes (1/1, v/v) to afford 0.69 g (64% yield) of the desired product as a colorless oil; MALDI-TOF-MS m/z (M+Na$^+$) calcd for $C_{24}H_{34}N_2O_5Na^+$ 453.5, obsd 453.3.

Boc-{(S)-Nip}$_3$-OBn 1.6. Via general procedure A, Boc {(S)-Nip-}$_2$OBn (0.37 g, 0.85 mmol) was Boc-deprotected and coupled with Boc-(S)-Nip-OH (0.19 g, 0.85 mmol).

After workup, the crude product was purified by column chromatography eluting with ethyl acetate/methanol (10/1, v/v) to afford 0.22 g (49% yield) of the desired product as a white foam; MALDI-TOF-MS m/z (M+Na$^+$) calcd for $C_{30}H_{43}N_3O_6Na^+$ 564.3, obsd 564.3.

Boc-{(S)-Nip}$_4$-OBn 1.7. Via general procedure A, Boc {(s)-Nip-}$_2$OBn (0.29 g, 0.62 mmol) was Boc-deprotected and coupled with Boc-{(S)-Nip}$_2$-OH (0.29 g, 0.85 mmol). After workup, the crude product was purified by column chromatography eluting with ethyl acetate/methanol (10/1, v/v) to afford 0.27 g (68% yield) of the desired product as a white foam; MALDI-TOF-MS m/z (M+Na$^+$) calcd for $C_{36}H_{52}N_4O_7Na^+$ 675.4, obsd 675.4.

Boc-{(S)-Nip}$_5$-OBn 1.8. Via general procedure A, Boc-(S)-Nip-OBn (88.4 mg, 0.28 mmol) was Boc-deprotected and coupled with Boc-{(S)-Nip}$_4$-OH (0.14 g, 0.28 mmol). After workup, the crude product was purified by column chromatography eluting with ethyl acetate/methanol (10/1, v/v) to afford 0.11 g (52% yield) of the desired product as a white foam; MALDI-TOF-MS m/z (M+Na$^+$) calcd for $C_{42}H_{61}N_5O_8Na^+$ 786.4, obsd 786.5.

Boc-{(S)-Nip}$_6$-OBn 1.9. Via general procedure A, Boc {(S)-Nip-}$_2$OBn (0.46 g, 1.1 mmol) was Boc-deprotected and coupled with Boc-{(S)-Nip}$_4$-OH (0.16 g, 0.3 mmol). After workup, the crude product was purified by column chromatography eluting with ethyl acetate/methanol (10/1, v/v) to afford 0.12 g (45% yield) of the desired product as a white foam; MALDI-TOF-MS m/z (M+Na$^+$) calcd for $C_{48}H_{70}N_6O_9Na^+$ 897.5, obsd 897.6.

The CD spectra of the nipecotic acid oligomers from the dimer to the hexamer are shown in FIG. 1. The data have been normalized for β-peptide concentration and number of amide groups. The CD spectrum of the trimer has a different maximum and minimum from the monomer and dimer. This suggests that the trimer is adopting a different secondary structure. As the oligomer is lengthened to tetramer and pentamer, the intensity of the spectra increase, which suggests that the secondary structure is becoming more stable. The hexamer has the same intensity as the pentamer, suggesting that adding further residues does not increase the stability of the Nip conformation. The isodichroic point at 218 nm suggests that only one distinct secondary structure is populated.

Circular dichroism data for 0.5 mM Nip pentamer in isopropanol as a function of temperature indicate that the Nip oligomers are thermally stable, and that only at 75° C. does the stability of the oligomer decrease (data not shown). Circular dichroism data for 0.5 mM Nip hexamer (25° C.) protected in methanol and deprotected in H$_2$O, pH=7.6 suggest that the same secondary structure is adopted in H$_2$O, with there being a small decrease in the stability of the structure (data not shown).

Pyrrolidine-3-Carboxylic Acid (PCA)

1. Synthesis of the Protected Monomer

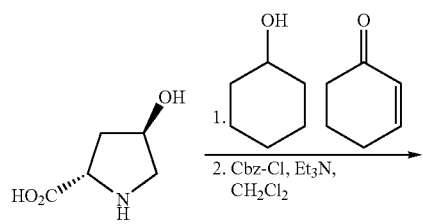

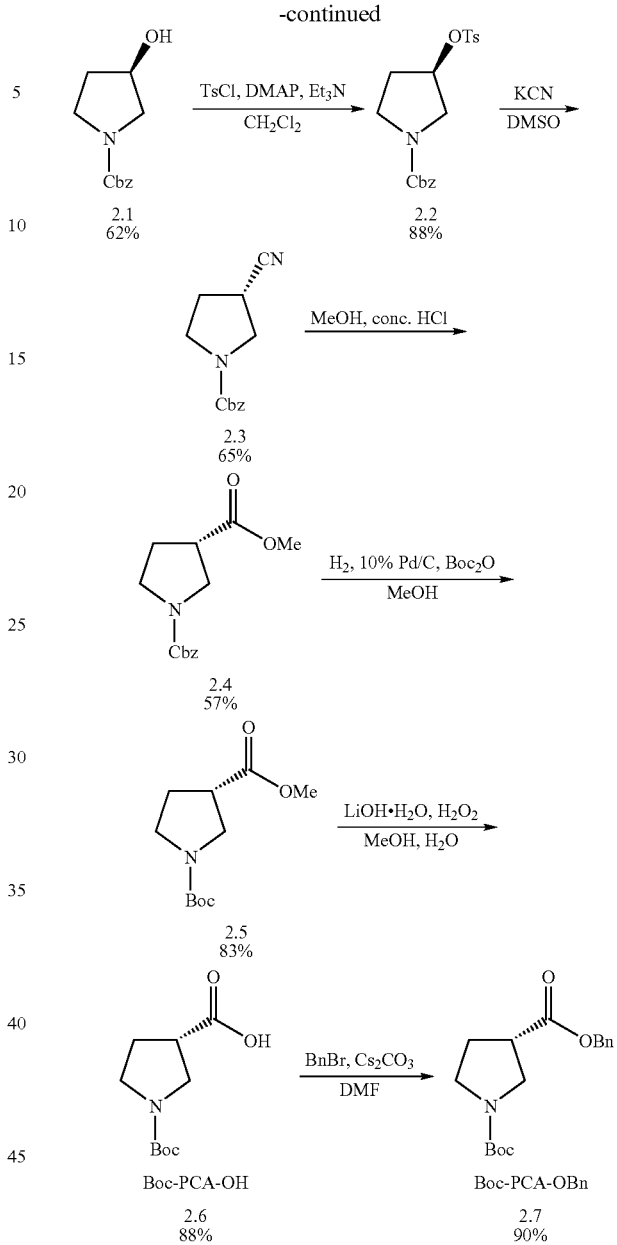

The synthesis of this monomer is an extension of that given in Klein et al. (1997), *Bio. & Med. Chem. Let.* 7:1773.

3-Hydroxy-(R)-Pyrrolidine. trans-4-Hydroxy-L-proline (13.11 g, 0.1 mol) was added to cyclohexanol (65 mL), followed by the addition of 2-cyclohexene-1-one (0.65 mL). The reaction mixture was heated at 180° C. until all solids were dissolved. The solution was cooled to room temperature and concentrated by vacuum rotary evaporation. The crude product was carried on to the next synthetic step without further purification.

3-Hydroxy-Cbz-(R)-Pyrrolidine 2.1. 3-Hydroxy-(R)-pyrrolidine (8.71 g, 0.1 mol) was dissolved in CH$_2$Cl$_2$ (260 mL) and cooled to 0° C. Triethylamine (33.5 mL, 0.24 mol) and benzyl chloroformate (14.9 mL, 0.11 mol) were added, and the resulting solution was stirred for 2 h at 0° C. The solution was gradually warmed to room temperature and allowed to stir overnight. The solution was washed with 1 M HCl, saturated NaHCO₃, and brine. The organic solution was dried over MgSO₄ and concentrated. The crude product was purified by column chromatography eluting with ethyl acetate to afford 13.7 g (62% yield, 2 steps) of the desired product as a purple oil.

3-Tosyl-Cbz-(R)-Pyrrolidine 2.2. 3-Hydroxy-Cbz-(R)-pyrrolidine (13.7 g, 0.06 mol) was dissolved in CH₂Cl₂ (250 mL) and cooled to 0° C. p-Toluenesulfonyl chloride (14.16 g, 0.07 mol), and triethylamine (20.7 mL, 0.15 mol) were added and the resulting solution was stirred for 4 h at 0° C. The solution was washed with 1 M HCl, saturated NaHCO₃, and brine. The organic solution was dried over MgSO₄ and concentrated. The crude product was purified by column chromatography eluting with ethyl acetate/hexanes (3/1, v/v) to afford 20.4 g (88% yield) of the desired product as an oil.

3-Cyano-Cbz-(S)-Pyrrolidine 2.3. 3-Tosyl-Cbz-(R)-pyrrolidine (20.4 g, 0.05 mol) was dissolved in DMSO (54 mL), followed by the addition of KCN (5.3 g, 0.08 mol). The reaction mixture was stirred for 5 h at 80° C. The solution was cooled to room temperature and brine/H₂O (90 mL) (1/1, v/v) was added. The aqueous solution was extracted with ethyl acetate. The organic extracts were dried over MgSO₄, and concentrated. The crude product was purified by column chromatography eluting with ethyl acetate/hexanes (1/1, v/v) to afford 8.13 g (65% yield) of the desired product as an oil.

Cbz(S)-PCA-OMe 2.4. 3-Cyano-Cbz-(S)-pyrrolidine (8.13 g, 35.3 mmol) was dissolved in methanol (35 mL), followed by the addition of concentrated HCl (35 mL). The solution was stirred for 3 days at room temperature. The solution was neutralized by NaHCO₃. The methanol was removed and the solution was diluted with H₂O (100 mL). The aqueous solution was extracted with CH₂Cl₂. The organic extracts were dried over MgSO₄ and concentrated. The crude product was purified by column chromatography eluting with ethyl acetate/hexanes (1/1, v/v) to afford 5.26 g (57% yield) of the desired product as a colorless oil.

Boc-(S)-PCA-OMe 2.5. Cbz-(S)-PCA-OMe (5.26 g, 20.0 mmol) was dissolved in methanol (0.1 M), 10% Pd/C (12% vol), and Boc₂O (5.67 g, 25.9 mmol) were added, and the solution was shaken on a Parr appartus for 12 h under psi of H₂. The solution was filtered through a plug of glass wool, and the filtrate was concentrated. The crude product was purified by column chromatography eluting with ethyl acetate/hexanes (1/1, v/v) to afford 3.79 g (83% yield) of the desired product as an colorless oil.

Boc-(S)-PCA-OH 2.6. Boc-(S)-PCA-OMe (2.52 g, 11.0 mmol) was dissolved in methanol (155 mL) and H₂O (54 mL) and the solution was cooled to 0° C. LiOH.H₂O (4.6 g, 0.11 mol) was added, followed by H₂O₂ (6.23 mL, 0.05 mol) and the solution was stirred for 15 h in the cold room at 5° C. While still cold, Na₂SO₃ (21 g, 0.17 mol) in H₂O (93 mL) was added. The methanol was removed and the solution was brought to pH 2 with 1 M HCl. The aqueous solution was extracted with methylene chloride. The organic extracts were dried over MgSO₄ and concentrated to afford 2.36 g (88% yield) of the desired product as a white solid.

Boc-(S)-PCA-OBn 2.7. Boc-(S)-PCA-OH (1.07 g, 4.9 mmol) was dissolved in DMF (50 mL). Cs₂CO₃ (1.62 g, 4.9 mmol) and benzyl bromide (0.63 mL, 5.2 mmol) were added, and the solution was stirred for 24 h at room temperature. The solution was then concentrated, and the residue was dissolved in H₂O. The aqueous solution was then extracted with ethyl acetate. The organic solution was dried over MgSO₄ and concentrated. The crude product was purified by column chromatography eluting with ethyl acetate/hexanes (1/3, v/v) to afford 1.52 g (90% yield) of the desired product as a white solid.

2. Oligomer Synthesis

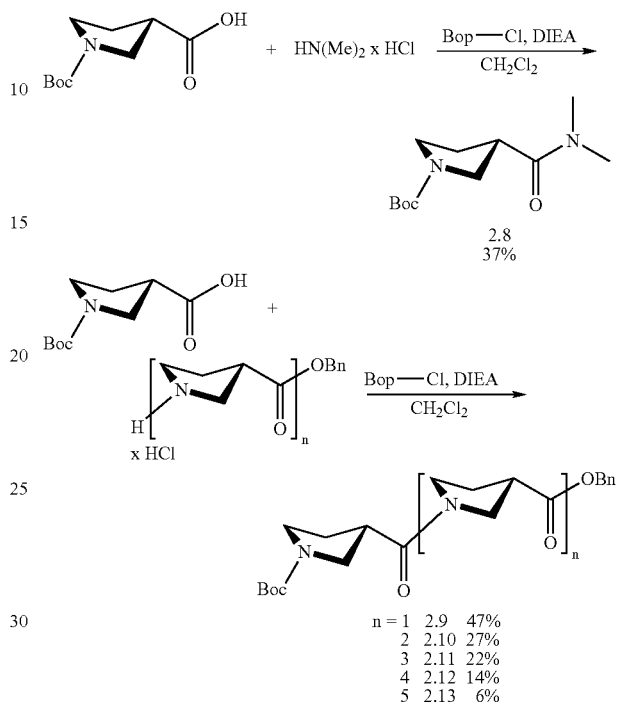

n = 1   2.9    47%
    2   2.10   27%
    3   2.11   22%
    4   2.12   14%
    5   2.13    6%

Boc-(S)-PCA-N(Me)₂ 2.8. Via general procedure A, HCl.N(Me)₂ (31.7 mg, 0.5 mmol) was coupled with Boc-(S)-PCA-OH (93.5 mg, 0.4 mmol). After workup, the crude product was purified by column chromatography eluting with ethyl acetate/hexanes (1/1, v/v) to afford 39.1 mg (37% yield) of the desired product as a colorless oil.

Boc-{(S)-PCA}₂-OBn 2.9. Via general procedure A, Boc-(S)-PCA-OBn (0.46 g, 1.5 mmol) was Boc-deprotected and coupled with Boc-(S)-PCA-OH (0.32 g, 1.5 mmol). After workup, the crude product was purified by column chromatography eluting with ethyl acetate/hexanes (3/1, v/v) to afford 0.28 g (47% yield) of the desired product as a colorless oil.

Boc-{(S)-PCA}₃-OBn 2.10. Via general procedure A, Boc-{(S)-PCA}₂-OBn (90 mg, 0.2 mmol) was Boc-deprotected and coupled with Boc-(S)-PCA-OH (48 mg, 0.2 mmol). After workup, the crude product was purified by column chromatography eluting with ethyl acetate/methanol (20/1, v/v) to afford 29.8 mg (27% yield) of the desired product as an colorless oil.

Boc-{(S)-PCA}₄-OBn 2.11. Via general procedure A, Boc-{(S)-PCA}₂-OBn (0.21 g, 0.5 mmol) was Boc-deprotected and coupled with Boc-{(S)-PCA}₂-OH (0.16 g, 0.5 mmol). After workup, the crude product was purified by column chromatography eluting with ethyl acetate/methanol (20/1, v/v) to afford 67.9 mg (27% yield) of the desired product as a white foam; MALDI-TOF-MS m/z (M⁺) calcd for C₃₂H₄₄N₄O₇Na 620.724, obsd 620.5.

Boc-{(S)-PCA}₅-OBn 2.12. Via general procedure A, Boc-{(S)-PCA}₃-OBn (0.10 g, 0.2 mmol) was Boc-deprotected and coupled with Boc-(S)-PCA-OH (36 mg, 0.2 mmol). After workup, the crude product was purified by column chromatography eluting with methylene chloride/methanol (20/1, v/v) to afford 16.3 mg (14% yield) of the desired product as a clear, glassy solid; MALDI-TOF-MS m/z (M⁺) calcd for $C_{37}H_{51}N_5O_8Na$ 716.841, obsd 716.5.

Boc-{(S)-PCA}$_6$-OBn 2.13. Via general procedure A, Boc-{(S)-PCA}$_4$-OBn (0.10 g, 0.2 mmol) was Boc-deprotected and coupled with Boc-{(S)-PCA}$_2$-OH (52 mg, 0.2 mmol). After workup, the crude product was purified by column chromatography eluting with methylene chloride/methanol (20/1, v/v) to afford 7.0 mg (6% yield) of the desired product as a clear, glassy solid; MALDI-TOF-MS m/z (M⁺) calcd for $C_{42}H_{58}N_6O_9Na$ 813.957, obsd 813.5.

Figure 2:
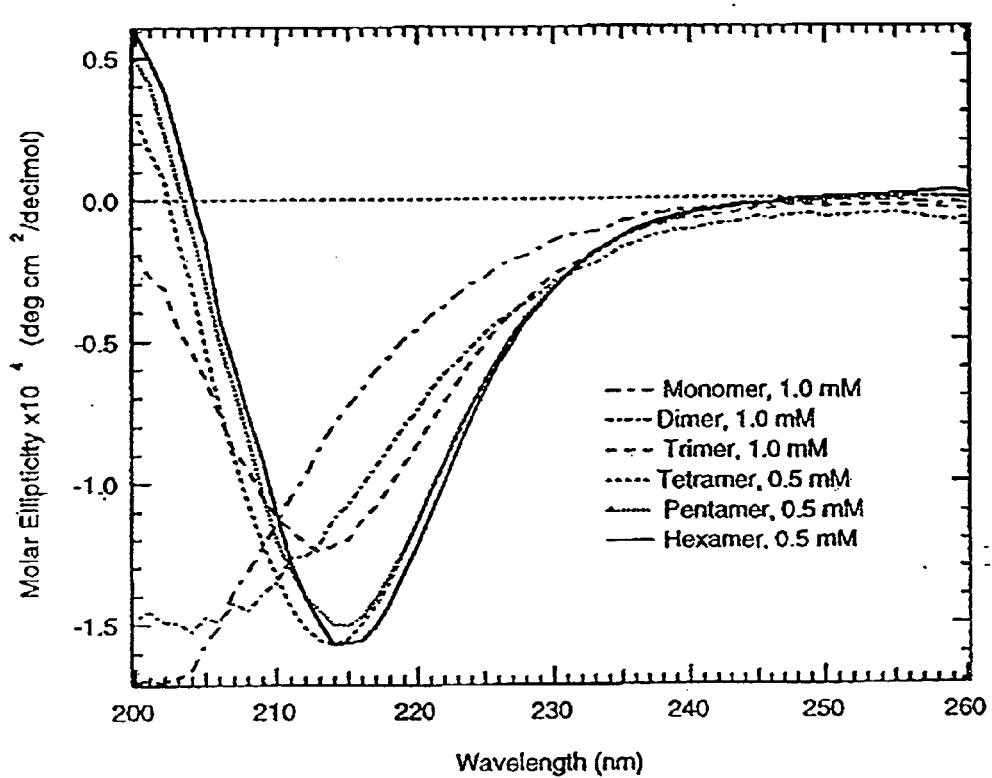
FIG. 2 depicts CD spectra (in methanol) for an oligomeric series (monomer to hexamer) of pyrrolidine-3-carboxylic acid oligomers.

Referring now to FIG. 2, circular dichroism data for PCA oligomers in methanol (25° C.) suggest that the monomer 2.8 and dimer 2.9 adopt a random conformation. The CD spectrum of the trimer 2.10 is different, which suggests that the oligomer is starting to adopt a distinct secondary structure. The CD spectra of the tetramer 2.11, pentamer 2.12, and hexamer 2.13 have a more intense signal than the trimer. This suggests that the secondary structure is more stable in going to the tetramer, but going to any higher oligomer, pentamer or hexamer, does not increase the structure's stability. An isodichroic point at 232 nm indicates that only one distinct secondary structure is being populated.

Circular dichroism data for 0.5 mM PCA pentamer 2.12 in isopropanol as a function of temperature, 25° C., 50° C., and 75° C., indicate that the oligomers are thermally stable. An increase in the temperature only modestly decreases the intensity of the oligomers (data not shown). Circular dichroism data for 0.5 mM PCA tetramer (25° C.) protected in methanol and deprotected in H$_2$O, pH=7.6, suggest that the PCA tetramer adopts the same secondary structure in H$_2$O; however, the stability of the oligomer has been decreased (data not shown).

Substituted Pyrrolidine-3-Carboxylic Acids

The reaction given below illustrates the synthesis of a pyrrolidine-3-carboxylic acid derivative bearing an amino group at the 4-position.

The final product, compound 58, can be converted to derivatives that can then be oligomerized in the same fashion as the other monomers described herein.

Compound 52: Compound 51 (2.0 g) and NaBH$_3$CN (0.54 g) were dissolved in methanol (40 ml), 1N HCl (aqueous) was added dropwise to maintain pH 3-4. After 15-20 minutes, pH change slowed. The mixture was stirred for an additional 1.0 hour, while 1N HCl was added occasionally to keep pH 3-4. Water (100 ml) was added. The mixture was extracted diethyl ether (3×150 ml). The extracts were washed with 1 N NaHCO3 (100 ml) and dilute brine (100 ml), dried over MgSO$_4$, and concentrated to give a colorless oil (1.9 g) in 95% yield. The product was used directly without further purification.

Compound 53: Compound 52 (1.9 g) and Ph$_3$P (2.8 g) were dissolved in toluene (anhydrous, 30 ml) under nitrogen. A solution of diethyl azodicarboxylate (1.5 ml) in toluene (10 ml) was subsequently introduced via syringe over 15 minutes. The reaction mixture was stirred under nitrogen at room temperature for 12 hours. The toluene was removed under reduced pressure. The residue was purified by column chromatography with ethyl acetate/hexane (3/7, v/v) as eluent to afford a colorless oil (1.6 g) in 91% yield.

Compound 54: Compound 53 (1.0 g) and R-(+)-α-methylbenzylamine (1.1 ml) were mixed with water (15 ml). The mixture was stirred at 55° C. for 67 hours. The mixture was taken up in diethyl ether (300 ml), and the aqueous layer was separated. The ether solution was washed with water (3×50 ml), dried over MgSO$_4$, and concentrated to give a slight yellow oil. The diastereometic isomers were separated by column chromatography with ethyl acetate/hexane (2/8, v/v) as eluent to give RSS (0.2 g) and RRR (0.34 g) in 51% overall yield.

Compound 55: Compound 54 (4.2 g) was dissolved in ethyl acetate (200 ml). 4N HCl in dioxane (4.35 ml) was added dropwise while stirring. A white precipitate resulted. The ethyl acetate was removed under reduced pressure, and the resulting white solid (4.6 g, 100%) was dried in vacuo.

Compound 56: Compound 55 (4.6 g) was dissolved in 95% ethanol (150 ml) in a hydrogenation flask. 10% Palladium on activated carbon (0.5 g) was added. The

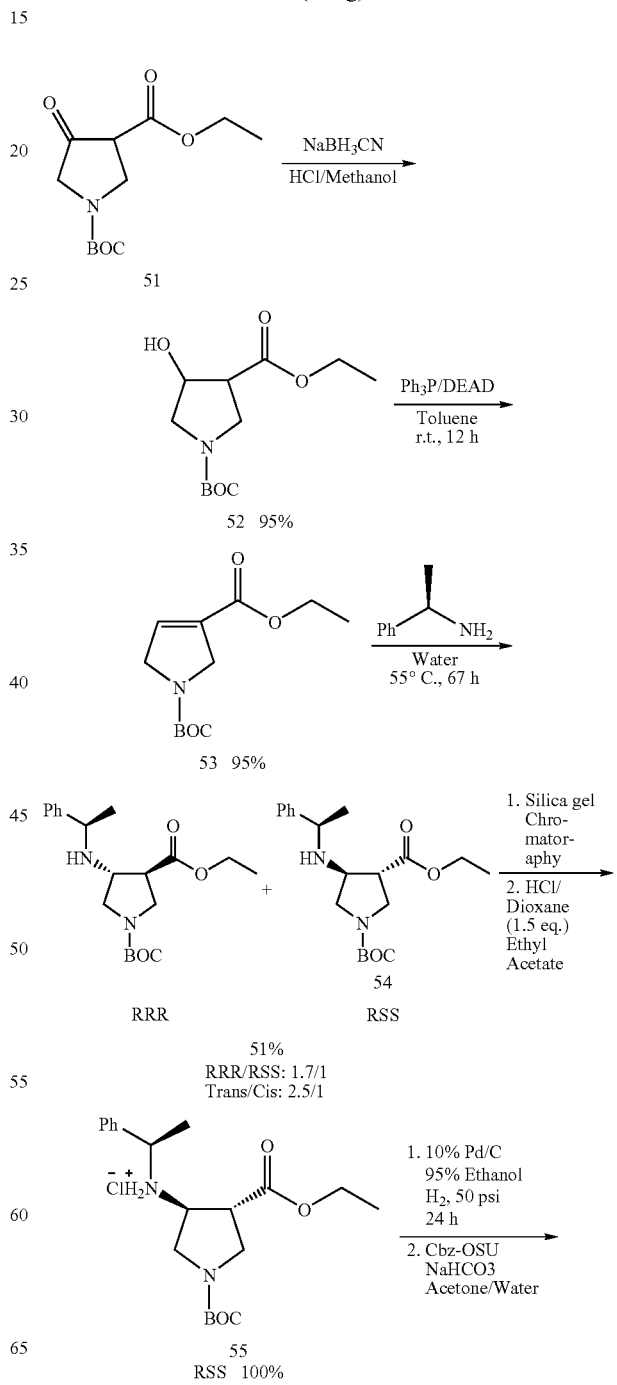

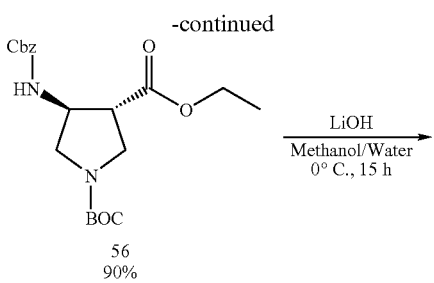

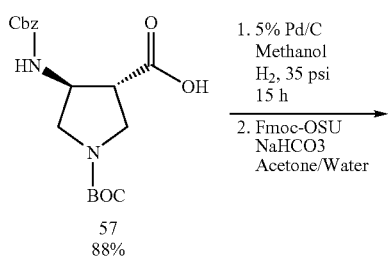

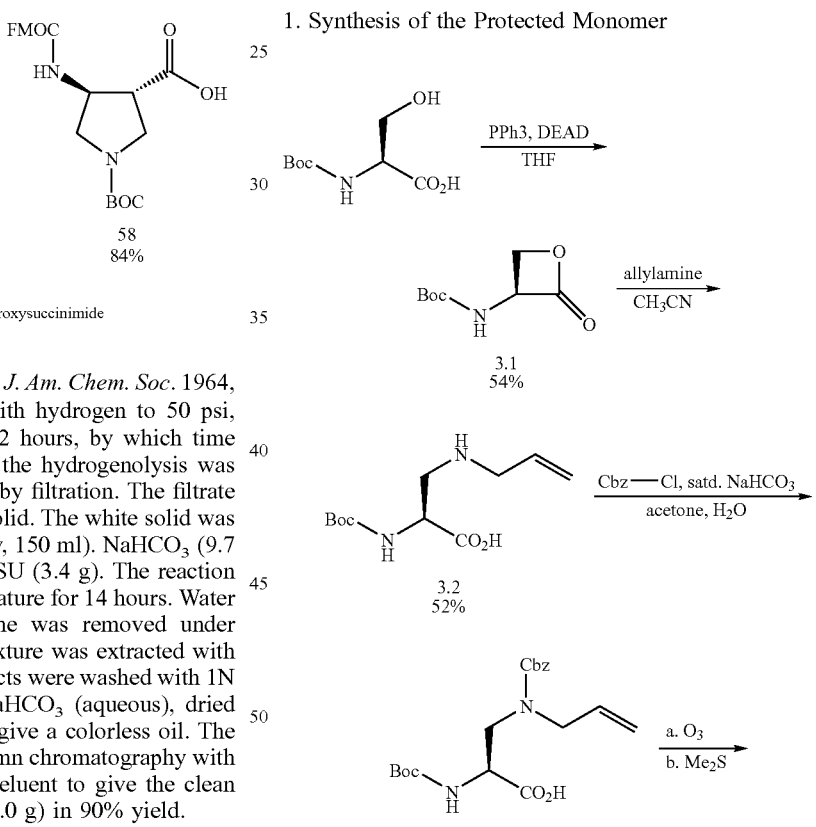

DEAD = Diethyl azodicarboxylate
Cbz-OSU = N-(Benzyloxycarbonyloxy)succinimide
Fmoc-OSU = 9-Fluorenylmethyloxycarbonyl-N-hydroxysuccinimide Starting material: Blake, J., et al., *J. Am. Chem. Soc.* 1964, 86, 5293 flask was pressurized with hydrogen to 50 psi, rocked at room temperature for 22 hours, by which time NMR spectroscopy indicated that the hydrogenolysis was complete. The Pd/C was removed by filtration. The filtrate was concentrated to give a white solid. The white solid was dissolved in acetone/water (2/1, v/v, 150 ml). NaHCO₃ (9.7 g) was added, followed by Cbz-OSU (3.4 g). The reaction mixture was stirred at room temperature for 14 hours. Water (100 ml) was added. The acetone was removed under reduced pressure. The aqueous mixture was extracted with ethyl acetate (3×200 ml). The extracts were washed with 1N HCl (3×100 ml) and saturated NaHCO₃ (aqueous), dried over MgSO₄, and concentrated to give a colorless oil. The crude product was purified by column chromatography with ethyl acetate/hexane (3/7, v/v) as eluent to give the clean product as a colorless sticky oil (4.0 g) in 90% yield.

Compound 57: Compound 56 (2.0 g) was dissolved in methanol/water (3/1, v/v, 115 ml), cooled to 0° C., LiOH.H20(2.4 g) was added. The mixture was stirred at 0° C. for 15 hours, by which time TLC indicated that the hydrolysis was complete. Saturated ammonium hydroxide (aqueous, 100 ml) was added. The methanol was removed under reduced pressure. The aqueous was acidified with 1N HCl to pH 3, extracted with ethyl acetate (3×200 ml). The extracts were washed with dilute brine (100 ml), dried over MgSO₄, concentrated to give a foamy solid (1.63 g, 88%), which was used directly without further purification.

Compound 58: Compound 57 (1.63 g) was dissolved in methanol (70 ml) in a hydrogenation flask. 5% Palladium on activated carbon (250 mg) was added. The flask was pressurized with hydrogen to 35 psi, rocked at room temperature for 15 hours, by which time NMR spectroscopy indicated that the hydrogenolysis was complete. The Pd/C was removed by filtration. The filtrate was concentrated to give a white solid. The white solid was dissolved in acetone/water (2/1, v/v, 90 ml), cooled to 0° C. NaHCO₃ (2.27 g) was added, followed by FMOC-OSu (1.83 g). The reaction mixture was stirred at 0° C. for 2 hours, then at room temperature for 28 hours. Water (50 ml) was added. The acetone was removed under reduced pressure. The aqueous was acidified with 1N HCl to pH 3, extracted with ethyl acetate (3×200 ml). The extracts were washed with dilute brine (100 ml), dried over MgSO₄, concentrated to give a foamy white solid. The crude white solid was purified by column chromatography with methanol/ethyl acetate (3/7, v/v) as eluent to give the clean product as a white solid (1.68 g) in 84% yield.

Piperazine Carboxylic Acid (PiCA)

1. Synthesis of the Protected Monomer

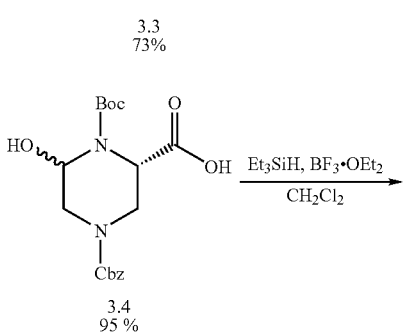

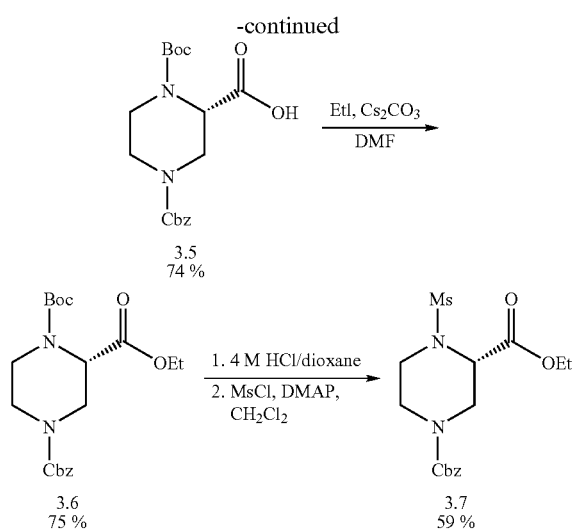

The synthesis of this monomer is an extension of that given in Patel et al. (1997), *J. Org. Chem.* 62:6439.

N-tert-Butoxycarbonyl-L-Serine-β-Lactone 3.1. A solution of triphenylphosphine (7.48 g, 28.5 mmol) in anhydrous THF (110 mL) was stirred under $N_2$, cooled to −78° C., and dimethylazodicarboxylate (4.83 mL, 30.7 mmol) was added dropwise. The mixture was stirred for 10 min, and a solution of Boc-serine (4.5 g, 21.9 mmol) in THF (110 mL) was added dropwise. After the addition, stirring was continued at −78° C. for 30 min, and for an additional 3 h after the cooling bath had been removed. The solution was concentrated, and the residue was purified by column chromatography eluting with hexanes/ethyl acetate (2/1, v/v) to afford 2.21 g (54% yield) of the desired product as a white solid.

(S)-$N^2$-(tert-Butoxycarbonyl)-$N_3$-(2-propenyl)-2,3-diaminopropanoic acid 3.2. A N-tert-Butoxycarbonyl-L-serine-β-lactone (2.21 g, 11.8 mmol) in acetonitrile (224 mL) was added dropwise to a stirred solution of allylamine (21.9 mL, 0.29 mmol) in acetonitrile (448 mL). The solution was stirred for 2 h at room temperature and then concentrated. The solid residue was slurried with acetonitrile and filtered to afford 1.51 g (52% yield) of the desired product as a white solid.

(S)-$N^2$-(tert-Butoxycarbonyl)-$N^3$-(benzyloxycarbonyl)-$N^3$-(2-propenyl)-2,3-diaminopropanoic acid 3.3. A solution of (S)-$N^2$-(tert-Butoxycarbonyl)-$N_3$-(2-propenyl)-2,3-diaminopropanoic acid (2.80 g, 11.4 mmol) in saturated $NaHCO_3$ (36 mL) and $H_2O$ (5 mL) was treated dropwise with a solution of benzyl chloroformate (1.84 mL, 12.8 mmol) in acetone (2.5 mL). The cloudy reaction mixture was stirred for 2 h. The resulting solution was partitioned between diethyl ether (130 mL) and $H_2O$ (65 mL). The aqueous layer was cooled in an ice bath, brought to pH 2 with 1 M HCl, and extracted with ethyl acetate. The organic extracts were dried over $MgSO_4$ and concentrated to afford 3.15 g (73% yield) of the desired product as a colorless oil.

(S)-$N^1$-(tert-butoxycarbonyl)-$N^4$-(benzyloxycarbonyl)-Piperazine Carboxylic Acid 3.5. A solution of (S)-$N^2$-(tert-Butoxycarbonyl)-$N^3$-(benzyloxycarbonyl)-$N^3$-(2-propenyl)-2,3-diaminopropanoic acid (3.15 g, 8.3 mmol) in methylene chloride (110 mL) and methanol (11 mL) was cooled to −78° C. under $N_2$. Ozone was passed through the solution until a pale blue color persisted (6 psi $O_2$, 90 V, 20 min). The excess ozone was purged by bubbling $N_2$ through the solution for 15 min. Dimethyl sulfide (11 mL) was added, and the solution was allowed to warm gradually to room temperature overnight. After 20 h, the reaction mixture was diluted with methylene chloride (200 mL) and washed with brine. The organic layer was dried over $MgSO_4$ and concentrated to afford 3.02 g (95% yield) of the desired product as a yellow foam.

The crude material and triethylsilane (1.4 mL, 8.8 mmol) in methylene chloride (200 mL) under $N_2$ were cooled to −78° C. and treated dropwise with boron trifluoride diethyl etherate (1.11 mL, 8.8 mmol). After 30 min, more triethylsilane (1.4 mL, 8.8 mmol) and boron trifluoride diethyl etherate (1.11 mL, 8.8 mmol) were added in a similar fashion. The reaction mixture was stirred for 2 h at −78° C., brine was added, and the cold mixture was extracted with methylene chloride. The organic extracts were dried over $MgSO_4$ and concentrated. The crude product was purified by column chromatography eluting with methylene chloride/ethyl acetate/acetic acid (2/1/0.03, v/v/v) to afford 2.13 g (74% yield) of the desired product as a white solid.

(S)-$N^1$-(tert-butoxycarbonyl)-$N^4$-(benzyloxycarbonyl)-Piperazine Ethyl Ester 3.6. (S)-$N^1$-(tert-butoxycarbonyl)-$N^4$-(benzyloxycarbonyl)-piperazine carboxylic acid (4.66 g, 12.8 mmol) was dissolved in DMF (128 mL). $Cs_2CO_3$ (4.37 g, 13.4 mmol) and ethyl iodide (1.23 mL, 15.3 mmol) were added and the reaction mixture was stirred for 24 h at room temperature. The reaction mixture was concentrated, and the residue was dissolved in $H_2O$. The aqueous solution was extracted with ethyl acetate. The organic layer was dried over $MgSO_4$ and concentrated. The crude product was purified by column chromatography eluting with ethyl acetate/hexanes (1/1, v/v) to afford 3.77 g (75% yield) of the desired product as an oil.

(S)-$N^1$-(mesyl)-$N^4$-(benzyloxycarbonyl)-Piperazine Ethyl Ester 3.7. (S)-$N^1$-(tert-butoxycarbonyl)-$N^4$-(benzyloxycarbonyl)-Piperazine ethyl ester (3.77 g, 9.6 mmol) was dissolved in 4 N HCl/dioxane and stirred for 2 h at room temperature. The reaction mixture was concentrated under a stream of $N_2$, then on the vacuum line. The residue was dissolved in methylene chloride and cooled to 0° C. Triethylamine (6.7 mL, 50 mmol) and DMAP (0.12 g, 1.0 mmol) were added, followed by methanesulfonyl chloride (1.5 mL, 19.2 mmol). The reaction solution was stirred for 24 h at room temperature. The reaction solution was then washed with brine, and the organic layer was dried over $MgSO_4$ and concentrated. The crude product was purified by column chromatography eluting with ethyl acetate/hexanes (1/1, v/v) to afford 2.1 g (59% yield) of the desired product as an oil.

2. Oligomer Synthesis

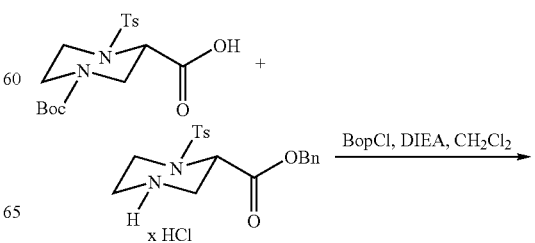

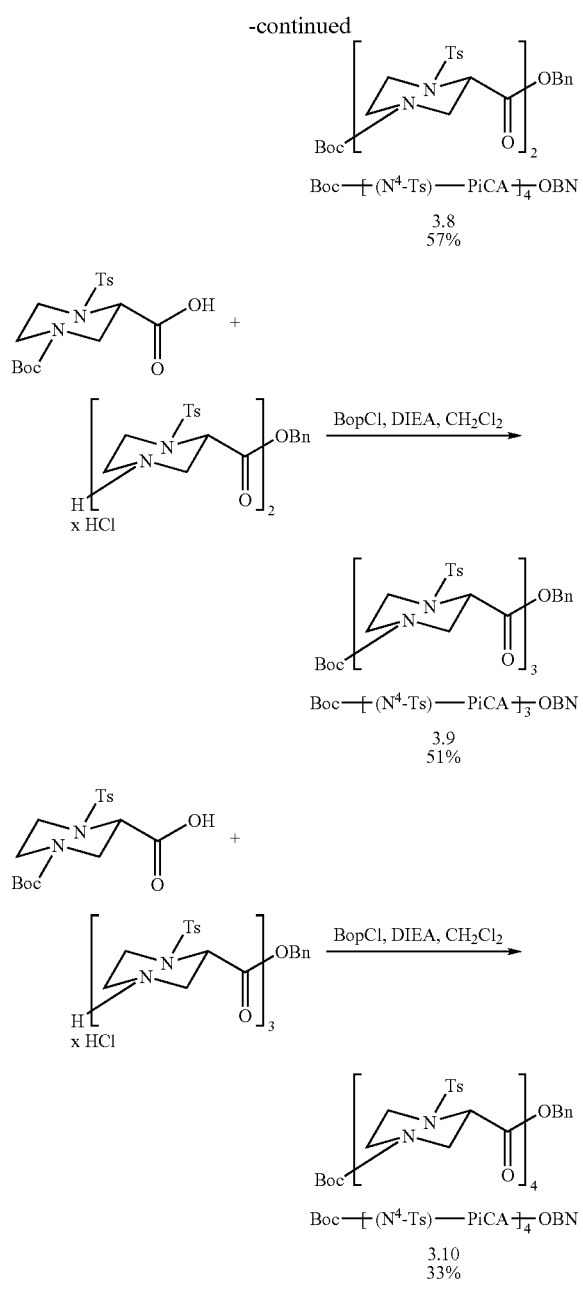

Boc-{(N⁴-Ts)-PiCA}₂-OBn 3.8. Via general procedure A, Boc-{(N⁴-Ts)-PiCA}-OBn (0.15 g, 0.3 mmol) was Boc-deprotected and coupled with Boc-{(N⁴-Ts)-PiCA}-OH (0.12 g, 0.3 mmol). After workup, the crude product was purified by column chromatography eluting with ethyl acetate/hexanes (1/1, v/v) to afford 0.13 g (57% yield) of the desired product as a colorless oil.

Boc-{(N⁴-Ts)-PiCA}₃-OBn 3.9. Via general procedure A, Boc-{(N⁴-Ts)-PiCA}₂-OBn (0.11 g, 0.2 mmol) was Boc-deprotected and coupled with Boc-{(N⁴-Ts)-PiCA}-OH (58.3 mg, 0.2 mmol). After workup, the crude product was purified by column chromatography eluting with ethyl acetate/hexanes (1/1, v/v) to afford 78 mg (51% yield) of the desired product as a white foam.

Boc-{(N⁴-Ts)-PiCA}₄-OBn 3.10. Via general procedure A, Boc-{(N⁴-Ts)-PiCA}₃-OBn (65.2 mg, 0.1 mmol) was Boc-deprotected and coupled with Boc-{(N⁴-Ts)-PiCA}-OH (24.9 mg, 0.1 mmol). After workup, the crude product was purified by column chromatography eluting with ethyl acetate/hexanes (1/1, v/v) to afford 25 mg (33% yield) of the desired product as a white foam.

Circular dichroism data for (N⁴-Ts)-PiCA oligomers in methanol (25° C.) suggest that the tetramer adopts a distinct secondary structure, which is different from the structure adopted by the dimer and trimer.

cis-5-Methoxymethyl-3-Pyrrolidine Carboxylic Acid (cis-5-MOM-PCA)

1. Synthesis of Protected Monomer

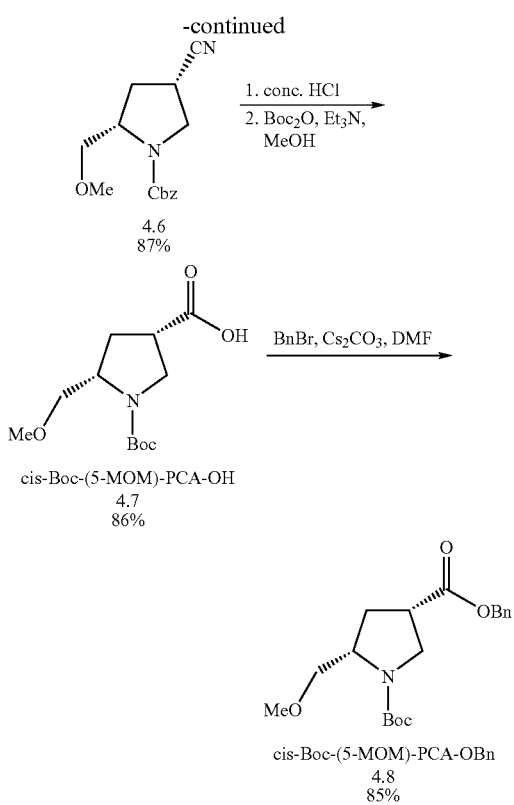

trans-4-Hydroxy-Cbz-L-Proline 4.1. Benzyl chloroformate (8.6 ML, 0.06 mol) was dissolved in acetone (12 mL), and this solution was added dropwise to a stirred solution of trans-4-Hydroxy-L-proline (6.56 g, 0.05 mol) in satd. NaHCO$_3$ (160 mL) and H$_2$O (24 mL). The resulting solution was stirred for 6 h at room temperature. The solution was washed with diethyl ether, and the organic layer was discarded. The aqueous layer was acidified with to pH 3 with 1 M HCl and extracted with ethyl acetate. The organic layer was dried over MgSO$_4$ and concentrated to afford 13.5 g (quantitative yield) of the desired product as an oil.

trans-4-TBDMSO-Cbz-L-Proline 4.2. trans-4-Hydroxy-Cbz-L-proline (13.5 g, 0.05 mol) was dissolved in DMF (190 mL), followed by the addition of imidazole (17.0 g, 0.25 mol) and TBDMS-Cl (22.6 g, 0.15 mol). The resulting solution was stirred for 12 h at room temperature. Methanol (150 mL) was added and the solution was stirred for 2 h. The solution was concentrated, the residue was dissolved in ethyl acetate and washed with 1 M HCl. The organic layer was dried over MgSO$_4$ and concentrated. The crude product was purified by column chromatography eluting with methylene chloride/ethyl acetate/acetic acid (2/1/0.03, v/v/v) to afford 18.01 g (95% yield) of the desired product as an oil.

trans-5-Hydroxylmethyl-3-TBDMSO-Cbz-Pyrrolidine 4.3. trans-4-TBDMSO-Cbz-L-proline (14.31 g, 0.04 mol) was dissolved in THF and added via cannula to a stirred solution of 2 M Me$_2$S.BH$_3$ in THF (48.0 mL, 0.09 mol). The resulting solution was stirred for 16 h at reflux. The reaction was then quenched with methanol (50 mL) and concentrated. The residued was dissolved in ethyl acetate and washed with brine. The organic layer was dried over MgSO$_4$ and concentrated. The crude product was purified by column chromatography eluting with hexanes/ethyl acetate (3/1, v/v) to afford 9.73 g (70% yield) of the desired product as an oil.

trans-5-Methoxymethyl-3-TBDMSO-Cbz-Pyrrolidine 4.4. trans-2-Hydroxylmethyl-4-TBDMSO-Cbz-pyrrolidine (5.02 g, 13.7 mmol) was dissolved in acetonitrile (13.7 mL), followed by the addition of iodomethane (8.55 mL, 0.14 mol) and Ag$_2$O (6.36 g, 27.5 mmol). The resulting reaction mixture was stirred for 12 h at reflux in the dark. The reaction mixture was then filtered through celite and the celite was washed with acetonitrile. The filtrate was concentrated. The crude product was purified by column chromatography eluting with hexanes/ethyl acetate (3/1, v/v) to afford 4.05 g (78% yield) of the desired product as an oil.

trans-5-Methoxymethyl-3-Tosyl-Cbz-Pyrrolidine 4.5. trans-2-Methoxymethyl-4-TBDMSO-Cbz-pyrrolidine (8.99 g, 23.6 mmol) was dissolved in THF (237 mL), followed by the addition of 1 M TBAF in THF (23.7 mL, 23.7 mmol). The resulting solution was stirred for 3 h at room temperature. The reaction was quenched with satd. NH$_4$Cl. The solution was concentrated, the residue dissolved in ethyl acetate and washed with brine. The organic layer was dried over MgSO$_4$ and concentrated. The residue was dissolved in methylene chloride (230 mL) and cooled to 0° C. DMAP (3.37 g, 27.6 mmol) and triethylamine (7.7 mL, 66.2 mmol) were added, followed by p-toluenesulfonyl chloride (5.26 g, 27.6 mmol). The reaction solution was stirred for 12 h at room temperature. The solution was washed with brine and the organic layer was dried over MgSO$_4$ and concentrated. The crude product was purified by column chromatography eluting with hexanes/ethyl acetate (2/1, v/v) to afford 8.67 g (90% yield) of the desired product as an oil.

cis-5-Methoxymethyl-3-Cyano-Cbz-Pyrrolidine 4.6. trans-5-Methoxymethyl-3-tosyl-Cbz-pyrrolidine (3.55 g, 8.8 mmol) was dissolved in DMSO (8.8 mL). Finely ground NaCN(0.65 g, 13.2 mmol) was added, and the resulting reaction mixture was stirred 4 h at 80° C. The solution was cooled to room temperature, diluted with H$_2$O (9 mL) and brine (9 mL), and extracted with ethyl acetate. The organic extracts were dried over MgSO$_4$ and concentrated. The crude product was purified by column chromatography eluting with hexanes/ethyl acetate (2/1, v/v) to afford 2.09 g (87% yield) of the desired product as an oil.

cis-5-Methoxymethyl-Boc-3-Pyrrolidine Carboxylic Acid {cis-Boc-(5-MOM)-PCA-OH} 4.7. cis-5-Methoxymethyl-3-cyano-Cbz-pyrrolidine (1.71 g, 6.2 mmol) was dissolved in concentrated HCl and stirred for 12 h at 50° C. The solution was cooled to room temperature and neutralized with NaHCO$_3$. The solution was concentrated, and the residue was dissolved in methanol (62 mL). Triethylamine (2.6 mL, 18.7 mmol) and Boc$_2$O (1.63 g, 7.5 mmol) were added, and the solution was stirred 12 h at 50° C. The solution was concentrated and the residue was dissolved in H$_2$O. The aqueous solution was washed with diethyl ether, and the organic layer was discarded. The aqueous layer was acidified with to pH 3 with 1 M HCl, and extracted with ethyl acetate. The organic layer was dried over MgSO$_4$ and concentrated to afford 1.40 g (86% yield) of the desired product as an oil.

cis-5-Methoxymethyl-Boc-3-Pyrrolidine Benzyl Ester Acid {cis-Boc-(5-MOM)-PCA-OBn} 4.8. cis-5-Methoxymethyl-Boc-3-pyrrolidine carboxylic acid (1.4 g, 5.3 mmol) was dissolved in DMF (26.5 mL). Cs$_2$CO$_3$ (1.73 g, 5.3 mmol) and benzyl bromide (0.76 mL, 6.4 mmol) were added, and the reaction mixture was stirred 24 h at room temperature.

The reaction mixture was concentrated, and the residue was dissolved in H₂O. The aqueous solution was extracted with ethyl acetate. The organic layer was dried over MgSO₄ and concentrated. The crude product was purified by column chromatography eluting with ethyl acetate/hexanes (1/1, v/v) to afford 1.88 g (85% yield) of the desired product as an oil.

2. Oligomer Synthesis

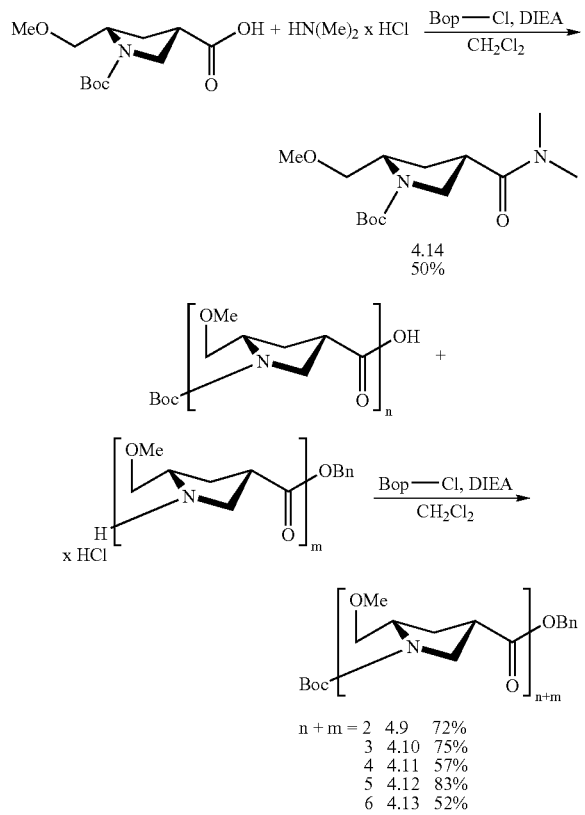

n + m = 2  4.9   72%
        3  4.10  75%
        4  4.11  57%
        5  4.12  83%
        6  4.13  52%

Boc-{(cis-5-MOM)-PCA}₂-OBn 4.9. Via general procedure B, cis-Boc-(5-MOM)-PCA-OBn (1.88 g, 5.38 mmol) was Boc-deprotected and coupled with cis-Boc-(5-MOM)-PCA-OH (1.40 g, 5.38 mmol). After workup, the crude product was purified by column chromatography eluting with ethyl acetate/hexanes (3/1, v/v) to afford 1.90 g (72% yield) of the desired product as an oil.

Boc-{(cis-5-MOM)-PCA}₃-OBn 4.10. Via general procedure B, cis-Boc-{(5-MOM)-PCA}₂-OBn (0.26 g, 0.54 mmol) was Boc-deprotected and coupled with cis-Boc-(5-MOM)-PCA-OH (0.13 g, 0.54 mmol). After workup, the crude product was purified by column chromatography eluting with ethyl acetate/methanol (20/1, v/v) to afford 0.25 g (75% yield) of the desired product as a white foam.

Boc-{(cis-5-MOM)-PCA}₄-OBn 4.11. Via general procedure B, cis-Boc-{(5-MOM)-PCA}₂-OBn (0.26 g, 0.54 mmol) was Boc-deprotected and coupled with cis-Boc-{(5-MOM)-PCA}₂-OH (0.20 g, 0.54 mmol). After workup, the crude product was purified by column chromatography eluting with ethyl acetate/methanol (15/1, v/v) to afford 0.24 g (57% yield) of the desired product as a white foam.

Boc-{(cis-5-MOM)-PCA}₅-OBn 4.12. Via general procedure B, cis-Boc-{(5-MOM)-PCA}₃-OBn (0.12 g, 0.18 mmol) was Boc-deprotected and coupled with cis-Boc-{(5-MOM)-PCA}₂-OH (0.09 g, 0.20 mmol). After workup, the crude product was purified by column chromatography eluting with methylene chloride/methanol (10/1, v/v) to afford 0.12 g (83% yield) of the desired product as a white foam.

Boc-{(cis-5-MOM)-PCA}₆-OBn 4.13. Via general procedure B, cis-Boc-{(5-MOM)-PCA}₄-OBn (0.13 g, 0.17 mmol) was Boc-deprotected and coupled with cis-Boc-{(5-MOM)-PCA}₂-OH (0.07 g, 0.17 mmol). After workup, the crude product was purified by column chromatography eluting with methylene chloride/methanol (10/1, v/v) to afford 70 mg (52% yield) of the desired product as a glassy solid.

Boc-(cis-5-MOM)-PCA-NMe₂ 4.14. Via general procedure B, Boc-cis-(5-MOM)-PCA-OBn (0.11 g, 0.41 mmol) was Boc-deprotected and coupled with dimethylamine hydrochloride (0.04 g, 0.49 mmol). After workup, the crude product was purified by column chromatography eluting with ethyl acetate/hexanes (3/1, v/v) to afford 57 mg (50% yield) of the desired product as an oil.

Figure 3:
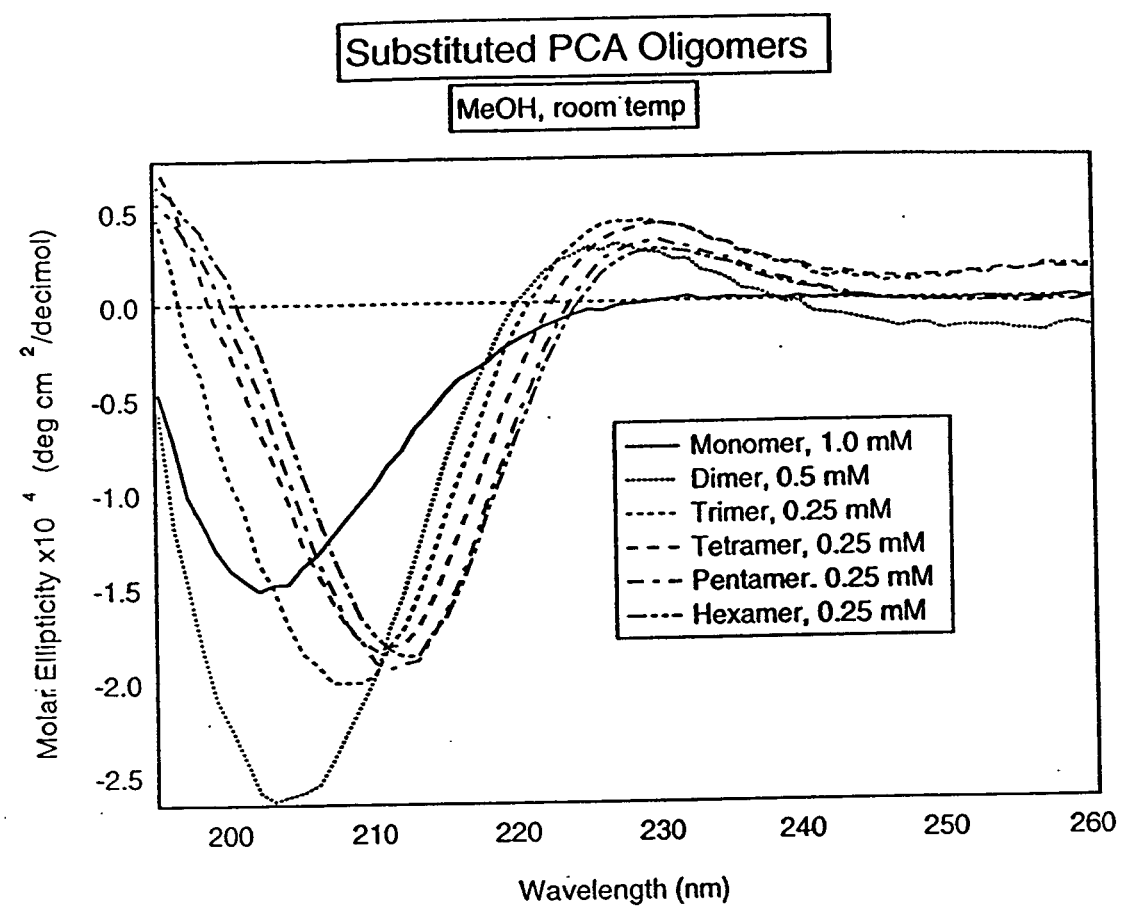
FIG. 3 depicts CD spectra (in methanol) for an oligomeric series (monomer to hexamer) of cis-5 methoxymethyl-3-pyrrolidine carboxylic acid ("cis-5-MOM-PCA").

CD spectra (25° C., methanol) for the oligomeric series from the monomer to the hexamer of cis-5-MOM)-PCA are shown in FIG. 3. The CD data indicate similar behavior to those described above for the Nip and PCA oligomer series: the "per residue"CD" shows a steady change from monomer to tetramer, and is essentially constant thereafter. As noted above, this appears to suggest that the secondary structure is maximized at the tetramer length.

Figure 4:
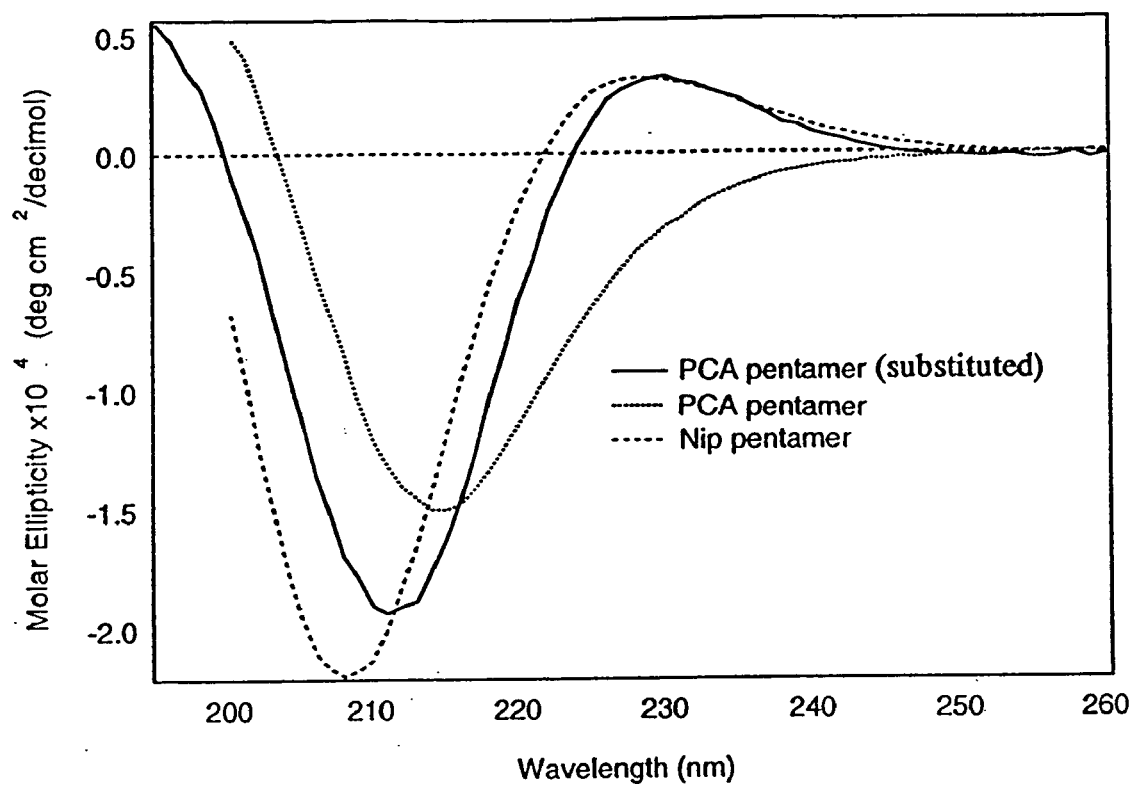
FIG. 4 depicts CD spectra (in methanol) comparing pentamers of the PCA, Nip, and cis-5-MOM-PCA compounds.

The CD spectra shown in FIG. 4 compare the pentamers of the PCA, Nip, and cis-5-MOM-PCA series of compounds. Interestingly, the cis-5-MOM-PCA pentamer CD curve is intermediate between the other two in terms of the minimum around 212 nm. This is slightly higher than the Nip pentamer and slightly lower than the PCA pentamer. While a detailed structural conclusion cannot be drawn from these data, they do suggest that all three pentamers may have related conformations.

Di-Substituted Carboxylic Acids

1. Synthesis of the Protected Monomer

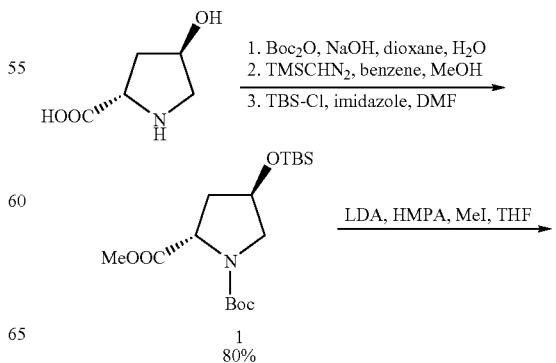

1
80%

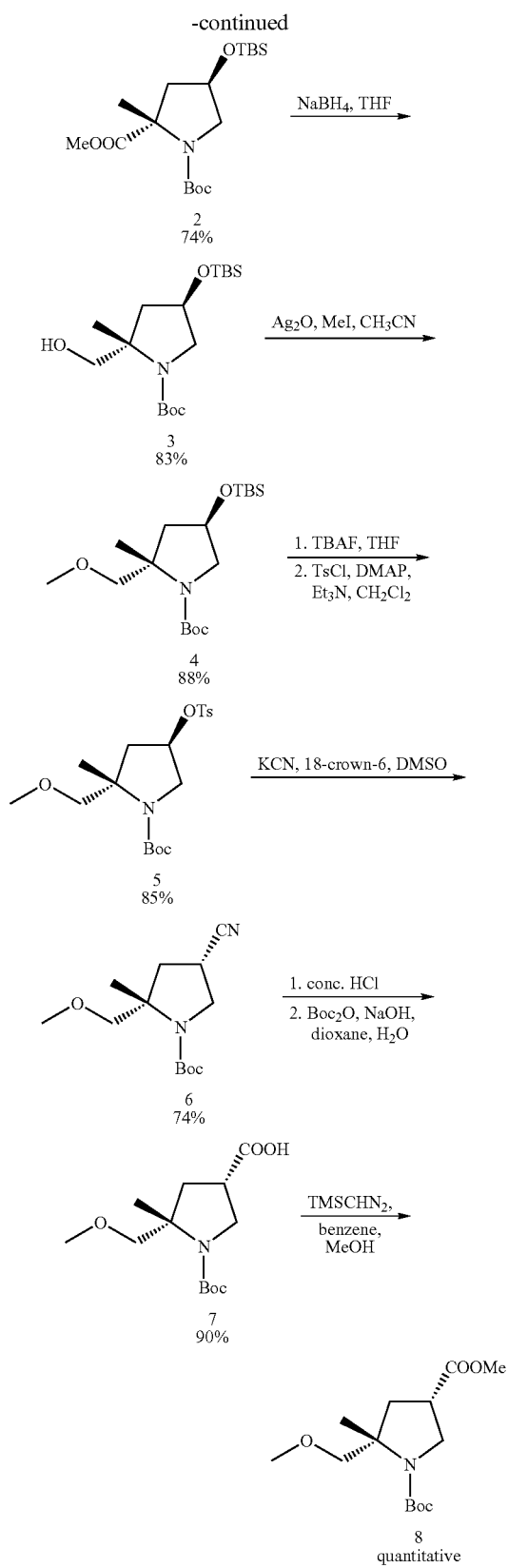

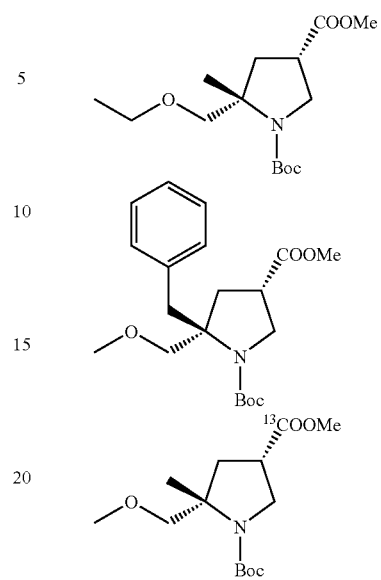

The following monomers have also been synthesized via a similar reaction scheme.

Compound 1. trans-4-Hydroxy-L-proline (13.11 g, 0.1 mol) was dissolved in 1M NaOH (120 mL) and cooled to 0° C. Boc$_2$O (24.0 g, 0.11 mol) dissolved in dioxane (120 mL) was added and the solution was stirred for 4 h at room temperature. Dioxane was removed via rotary evaporation and the resulting aqueous solution was washed with ether. The aqueous solution was then brought to pH 2 with 1 M HCl and extracted with ethyl acetate. The organic extracts were dried over MgSO$_4$ and concentrated to afford 21.3 g (92% yield) of the desired product as a white foam.

Boc-trans-4-hydroxy-L-proline (9.27 g, 0.04 mol) was dissolved in a 1M benzene/methanol (5/1, v/v) solution. 2M TMSCHN$_2$/hexanes was added dropwise and the resulting solution was stirred at room temperature for 1 h. The reaction solution was concentrated via rotary evaporation. The crude product was carried on to the next synthetic step without further purification.

Boc-trans-4-hydroxy-L-proline methyl ester (10.35 g, 0.04 mol) was dissolved in DMF (135 mL). Imidazole (13.6 g, 0.20 mol) was added, followed by the addition of tert-butyldimethylsilyl chloride (18.1 g, 0.12 mol) and the solution was stirred overnight at room temperature. DMF was removed via vacuum rotary evaporation and the residue was dissolved in ethyl acetate. The solution was washed with 1M HCl and brine. The organic solution was dried over MgSO$_4$ and concentrated. The crude product was purified by column chromatography eluting with hexanes/ethyl acetate (4/1, v/v) to afford 12.83 g (89% yield) of the desired product 1 as a colorless oil.

Compound 2. Diisopropyl amine (16.2 mL, 0.12 mol) was dissolved in THF (215 mL) and cooled to 0° C. 2.5M n-Butyllithium/hexanes was added and the solution was stirred for 30 minutes at 0° C. The solution was then cooled to −20° C. and HMPA (60 mL, 0.34 mol) was added. After 10 minutes, a solution of 1 (27.4 g, 0.076 mol) in THF (215 mL) was added dropwise. After addition the reaction solution was stirred from −20° C. to 0° C. The solution was then cooled to −78° C. and methyl iodide (23.7 mL, 0.38 mol) was added. The reaction solution was stirred for 2 h at −78° C. and then quenched with saturated NH$_4$Cl. The resulting solution was extracted with ethyl acetate. The organic extracts were dried over MgSO$_4$ and concentrated. The crude product was purified by column chromatography eluting with hexanes/ethyl acetate (6/1, v/v) to afford 21.09 g (74% yield) of the desired product 2 as a colorless oil. See Ohtake et al. (1999), Bull. Chem. Soc. Japan 72:2737.

Compounds 3. NaBH$_4$ (6.14 g, 0.16 mol) was added to a stirred solution of 2 (24.26 g, 0.065 mol) in THF (150 mL). The resulting solution was stirred at reflux for 4 h. MeOH (50 mL) was added over 1 h, and the solution was then diluted with H$_2$O. The organic solvents were removed via rotary evaporation and the resulting aqueous solution was extracted with ethyl acetate. The organic extracts were dried over MgSO$_4$ and concentrated. The crude product was purified by column chromatography eluting with hexanes/ethyl acetate (3/1, v/v) to afford 17.76 g (83% yield) of the desired product 3 as a colorless oil.

Compound 4. 3 (15.19 g, 0.046 mol) was dissolved in CH$_3$CN. Methyl iodide (28.7 mL, 0.46 mol) was added, followed by the addition of Ag$_2$O (25 g, 0.092 mol). The reaction mixture was stirred overnight at 55° C., and then filtered through celite. The resulting filtrate was concentrated and purified by column chromatography eluting with hexanes/ethyl acetate (4/1, v/v) to afford 13.88 g (88% yield) of the desired product 4 as a colorless oil.

Compound 5. 1M TBAF/THF (42 mL, 0.042 mol) was added dropwise to a solution of 4 (13.88 g, 0.04 mol) in THF (200 mL). The solution was stirred for 3 h at room temperature and the quenched with saturated NH$_4$Cl. The organic solvent was removed via rotary evaporation, and the resulting aqueous solution was extracted with ethyl acetate. The organic extracts were dried over MgSO$_4$ and concentrated. The crude product was carried on to the next synthetic step without further purification.

The crude product was dissolved in CH$_2$Cl$_2$ (200 mL) and cooled to 0° C. DMAP (5.9 g, 0.049 mol) and triethylamine (13.5 mL, 0.099 mol) were added, followed by p-toluenesulfonyl chloride (8.8 g, 0.049 mol), and the resulting solution was stirred overnight at room temperature. The solution was washed with 1M HCl, and brine. The organic solution was dried over MgSO$_4$ and concentrated. The crude product was purified by column chromatography eluting with hexanes/ethyl acetate (4/1, v/v) to afford 13.76 g (85% yield) of the desired product 5 as a colorless oil.

Compound 6. 5 (13.76 g, 0.034 mol) was dissolved in DMSO (17 mL). 18-Crown-6 (5 eq) and finely ground KCN (5 eq) were added and the reaction mixture was stirred for 6 h at 80° C. The reaction solution was diluted with H$_2$O (17 mL) and then extracted with ethyl acetate. The organic solution was dried over MgSO$_4$ and concentrated. The crude product was purified by column chromatography eluting with hexanes/ethyl acetate (4/1, v/v) to afford 13.76 g (69% yield) of the desired product 6 as a colorless oil.

Compound 7. 6 (4.34 g, 0.017 mol) was dissolved in concentrated HCl (68 mL) and stirred 6 h at 50° C. The solution was diluted with H$_2$O, neutralized with NaHCO$_3$, and concentrated. The crude product was carried on to the next synthetic step without further purification.

Triethylamine (9.5 mL, 0.068 mol) and Boc$_2$O (7.5 g, 0.034 mol) were added to a stirred solution of the resulting crude product in MeOH (170 mL). The reaction mixture was stirred overnight at reflux. The reaction mixture was diluted with H$_2$O, the MeOH was removed via rotary evaporation, and the resulting aqueous solution was washed with ether. The aqueous solution was then brought to pH 2 with 1 M HCl and extracted with ethyl acetate. The organic extracts were dried over MgSO$_4$ and concentrated to afford 3.55 g (76% yield) of 7 as the desired product as a white foam.

Compound 8. 7 (2.3 g, 8.4 mmol) was dissolved in a 1M benzene/methanol (5/1, v/v) solution. 2M TMSCHN$_2$/hexanes (4.4 mL, 8.8 mmol) was added dropwise and the resulting solution was stirred at room temperature for 1 h. The reaction solution was concentrated by rotary evaporation. The crude product was purified by column chromatography eluting with hexanes/ethyl acetate (1/1, v/v) to afford 2.4 g (quantitative yield) of the desired product 8 as a colorless oil.

2. Oligomer Synthesis

A. Synthesis of Free Amine

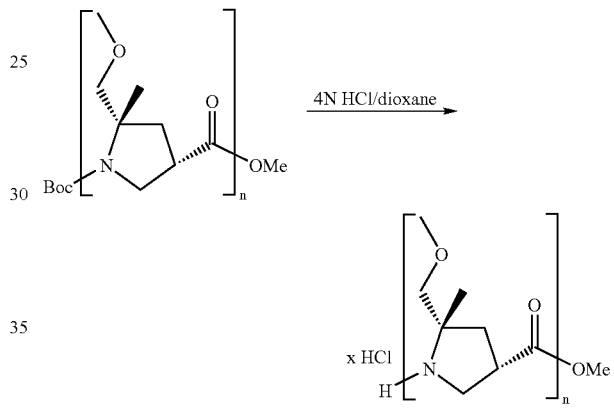

B. Synthesis of Boc Protected Amine

C. Synthesis of Isobutyl Amide

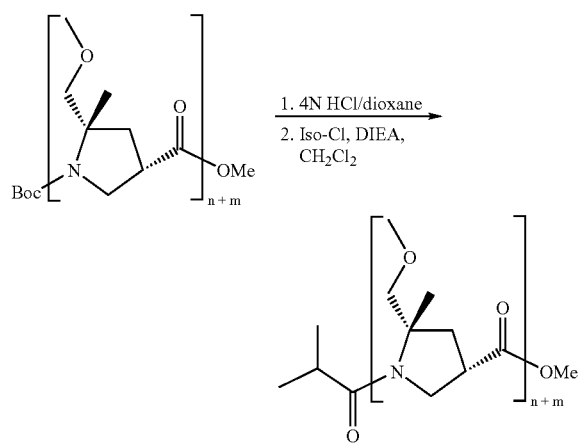

A. General procedure for synthesis of free amine. Boc-(disub PCA)$_n$-OMe was dissolved in 4N HCl/dioxane (2.5 eq.) The solution was stirred for 2 h, the solvent was removed under a stream of N$_2$, and the residue was dried under vacuum to give the desired product, HCl*H-(disub PCA)$_n$-OMe, as a white solid.

B. General procedure for synthesis of Boc protected amine. Boc-(disub PCA)$_m$-OH and HCl*H-(disub PCA)$_n$-OMe were dissolved in CH$_2$Cl$_2$ (0.1 M) and cooled to 0° C. BopCl (2.0 eq.) was added, followed by DIEA (5 eq.) The reaction mixture was stirred for 48 h at room temperature. The solution was washed with 1M HCl, saturated NaHCO$_3$, and brine. The organic solution was dried over MgSO$_4$ and concentrated. The crude product was purified by column chromatography to give the desired product, Boc-(disub PCA)$_{n+m}$-OMe.

C. General procedure for synthesis of isobutyl amide. Boc-(disub PCA)$_{n+m}$-OMe was dissolved in 4N HCl/dioxane (2.5 eq.) The solution was stirred for 2 h, the solvent was removed under a stream of N$_2$, and the residue was dried under vacuum to give the desired product, HCl*H-(disub PCA)$_{n+m}$-OMe, as a white solid. This residue was dissolved in CH$_2$Cl$_2$ and cooled to 0° C. Iso-Cl (2 eq.) was added, followed by DIEA (5 eq.) The reaction solution was stirred for 24 h at room temperature. The solution was washed with 1M HCl, saturated NaHCO$_3$, and brine. The organic solution was dried over MgSO$_4$ and concentrated. The crude product was purified by column chromatography to give the desired product, Iso-(disub PCA)$_{n+m}$-OMe.

D. Synthetic Yields.

|  | Dimer (%) | Trimer (%) | Tetramer (%) | Pentamer (%) |
|---|---|---|---|---|
| Boc carbamate | 66 | 14 | 28 | 55 |
| Isobutyl amide | 66 | 56 | 77 | 61 |

The synthesis of the free amine of each oligomer was assumed to be quantitative based on TLC analysis. Each oligomer was analyzed by MALDI-TOF-MS, $^1$H NMR, and $^{13}$C NM.

Figure 5:
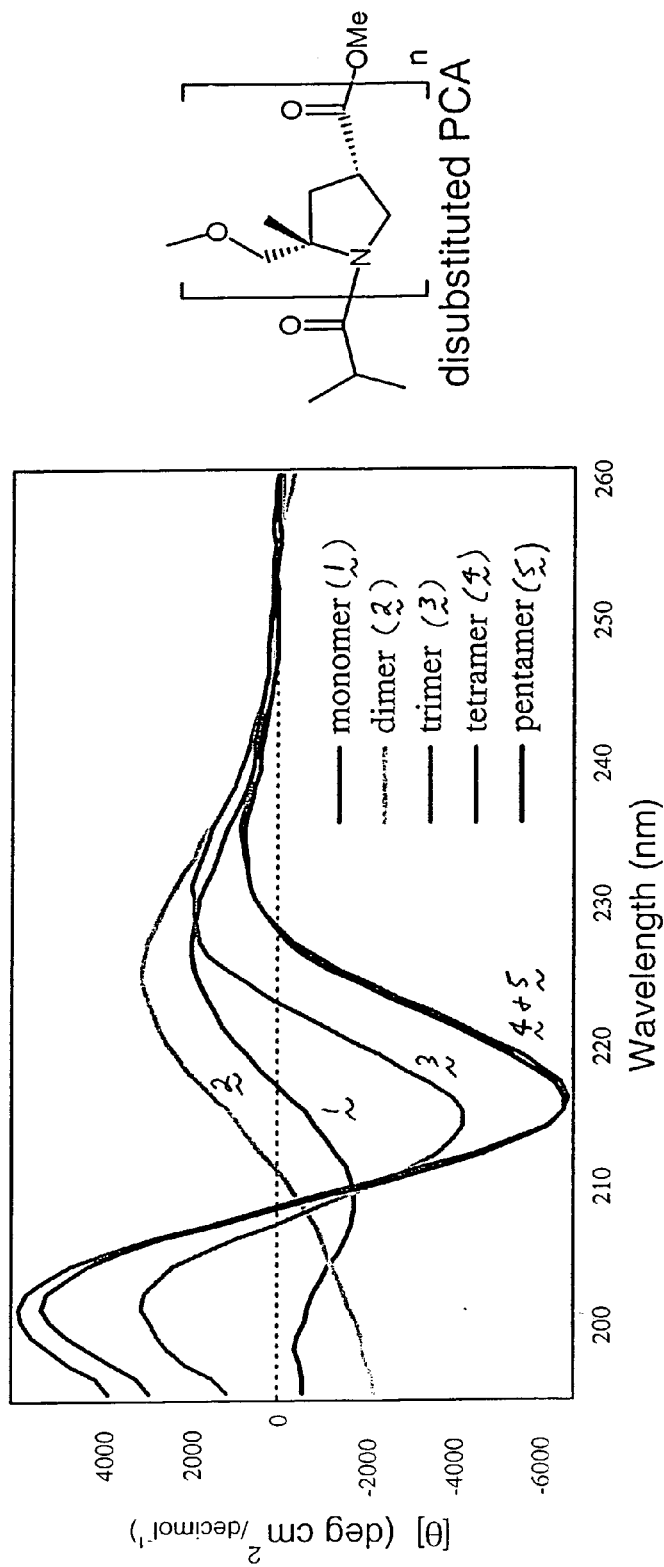
FIG. 5 depicts CD spectra (in methanol) for an oligomeric series (monomer to pentamer) of di-substituted PCA.

FIG. 5 is a series of CD spectra for the monomer through to the pentamer of the di-substituted PCA compound shown in the figure. As can be seen from comparing the trace for the trimer to the traces for the tetramer and pentamer (which are virtually superimposed), the minima for the tetramer and pentamer are greater in amplitude and shifted to a longer wavelength as compared to the minimum for the trimer. This indicates that the tetramer and pentamer adopt a distinct conformation in solution.

Figure 6:
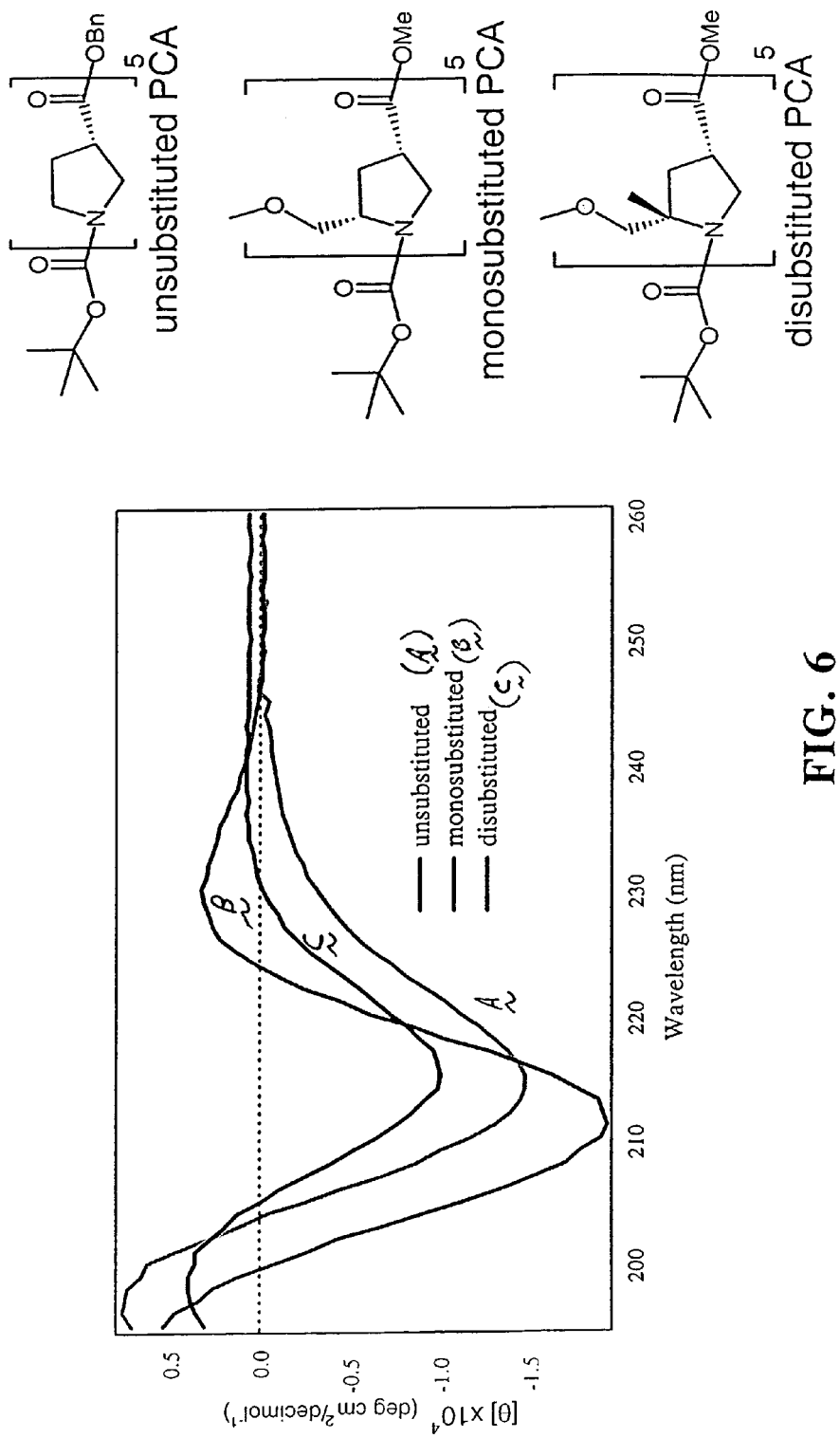
FIG. 6 depicts CD spectra (in methanol) comparing pentamers of unsubstituted PCA, mono-substituted PCA, and dis-substituted PCA.

Similarly, FIG. 6 is a series of CD spectra for unsubstituted PCA, mono-substituted PCA, and distubstituted PCA pentamers. All three spectra display a minimum consistent with the adoption of a definitive, likely helical, conformation in solution.

A likely cause for the spectra seen in the di-substituted compounds is steric hindrance between the substituents on the nitrogen heteroatom and the substituents on the di-substituted carbon atom of the ring. As shown in the following chemical structures, when the carbon adjacent the nitrogen heteroatom is unsubstituted, the nitrogen substituents are free to rotate and the compound exists in two distinct rotameric forms, as detected by NMR:

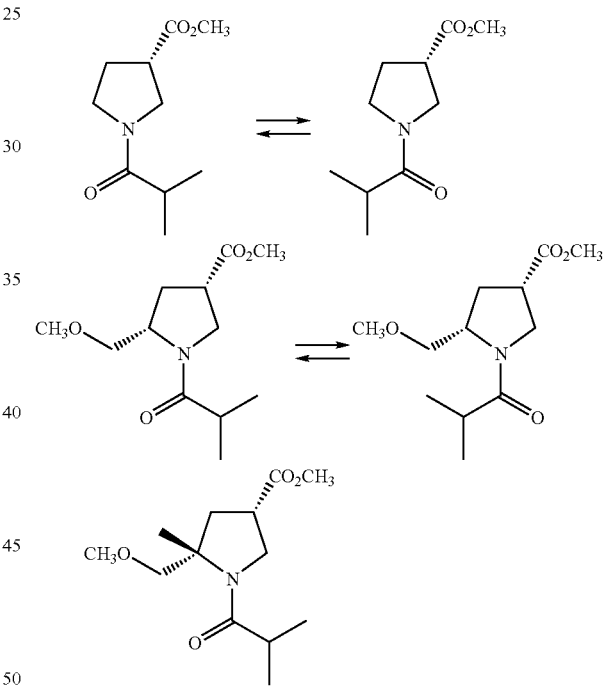

Similarly, when the carbon adjacent to the nitrogen heteroatom is only mon-substituted, rotamers are still seen in the NMR spectra.

However, when the carbon atom adjacent to the nitrogen heteroatom is di-substituted, steric hindrance prevents rotation about the exocyclic nitrogen-carbon bond and the compound thus exists in a single rotameric form, as shown above. That this is the case is shown by examining the NOE spectra of the subject compounds.

Figure 7:
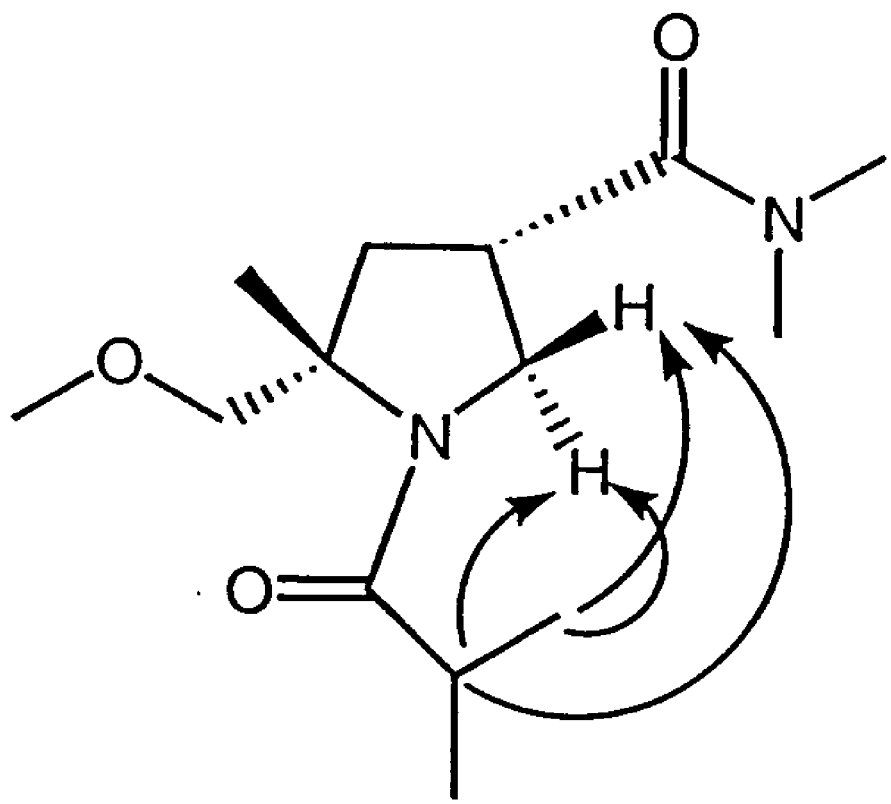
FIG. 7 is a chemical structure depicting the observed NOE signals in the di-substituted PCA.

FIG. 7 illustrates the observed NOE's for a di-substituted PCA according to the present invention. The arrows indicate observed NOE's. As can be seen in the figure, there is no observed NOE between the hydrogens of terminal methyl groups of the nitrogen substituent and the hydrogens present in the substituents on the di-substituted carbon atom of the ring. The lack of any observed NOE between these hydrogens indicates that the molecule must adopt the conformation shown in FIG. 7.

Figure 8:
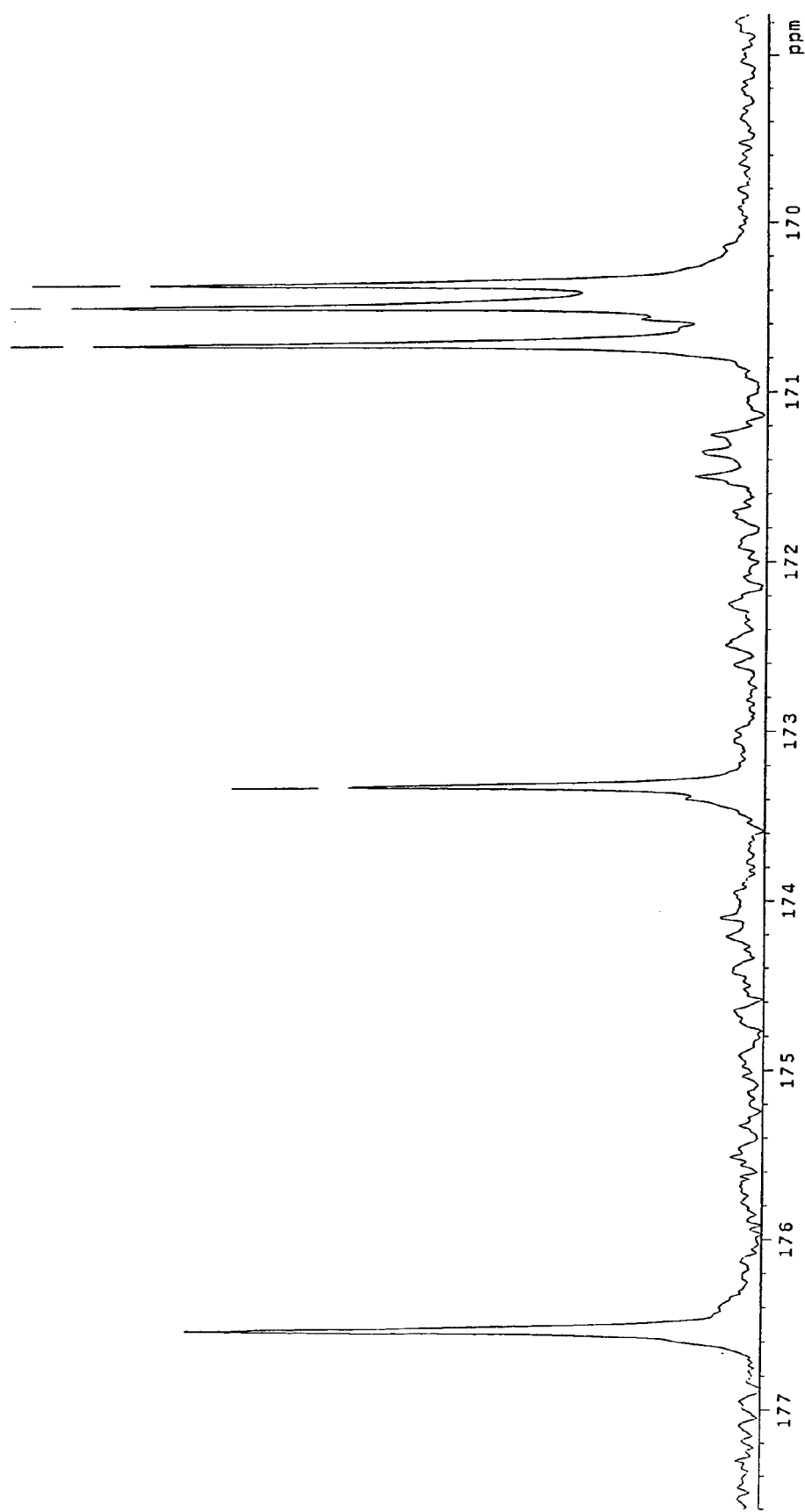
FIG. 8 is a $^{13}C$-NMR spectrum of the tetramer whose CD spectrum is shown in FIG. 5.

In corroborating these data is the $^{13}$C-NMR shown in FIG. 8. The spectrum is for that of the tetrameric compound depicted in FIG. 5. The spectrum, taken from the carbonyl region, shows five distinct peaks, corresponding to the three internal amides, the N-terminal amide, and the ester.

Figure 9:
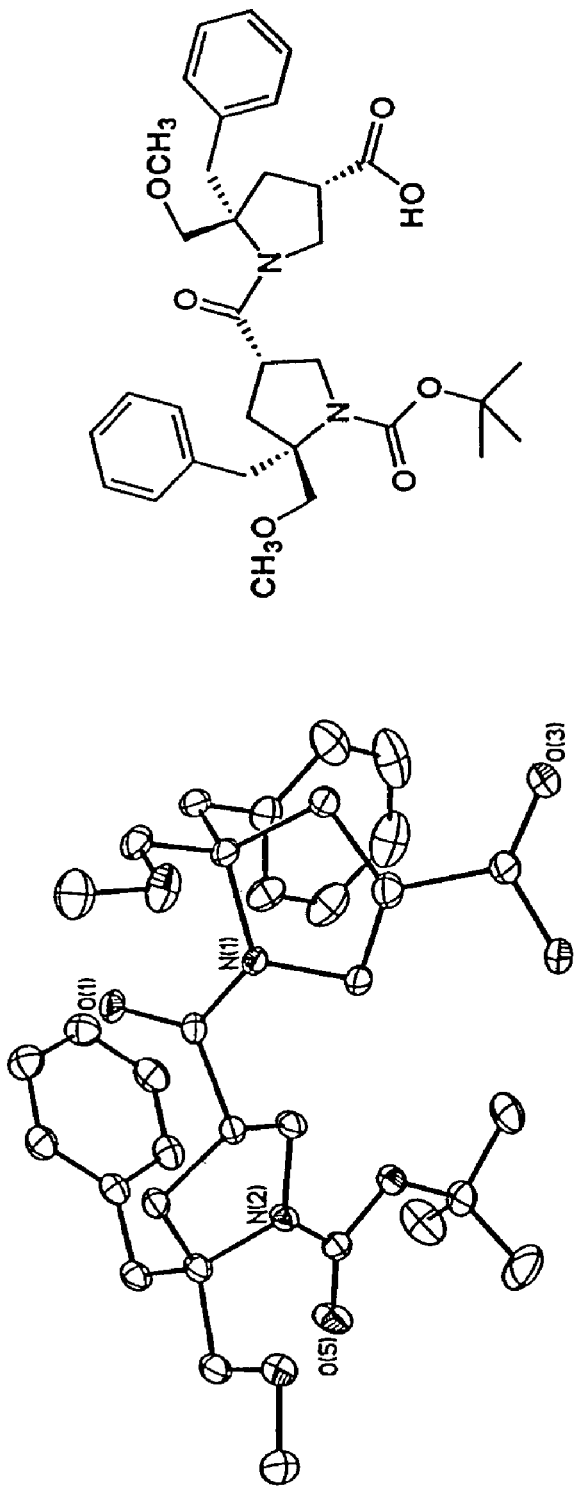
FIG. 9 is a crystal structure of a di-substituted PCA dimer.

FIG. 9 depicts the crystal structure for the di-substituted dimer shown in the figure. This structure confirms that there is a proper rotation about the amide bond connecting the two residues to yield a helical structure having roughly four residues per turn in longer oligomers.

Molecular Modeling Studies:

Computer Simulations of a $3_1$-Helix of trans-3-carboxy-4-methylpiperidine:

Because an oligomer of trans-3-carboxy-4-methylpiperidine (TCMP) can contain no intramolecular hydrogen bonds, a regular helical structure must be stabilized through intrinsic molecular preferences.

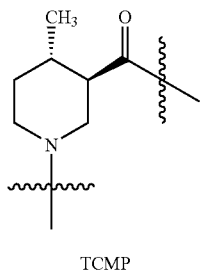

TCMP (1)

Thus, these conformational preferences must be determined before any helical structure can be evaluated. The three molecules shown below were constructed to determine the effect an alkyl substituent has on the rotation of the C2—C3—C(O)—N1' torsion. Each of these molecules was put through a dihedral drive simulation in MacroModel 6.0, using the AMBER*C force field and CHCl$_3$ GB/SA continuous solvation. See Mohamadi, F., Richards, N. G. J., Guida, W. C., Liskamp, R., Lipton, M., Caufield, C., Chang, G., Hendrickson, T., Still, W. C. *J. Comput. Chem.* 1990, 11, 440. (MacroModel—an Integrated Software System for Modeling Organic and Bioorganic Molecules Using Molecular Mechanics); Christianson, L. A. Thesis. University of Wisconsin-Madison, 1997; and Still, Tempczyk, Hawley and Hendrickson, *J. Am. Chem. Soc.* 1990, 112, 6127, respectively. For each of the simulations, the desired torsion was rotated from 0□°-360° in 10° increments and minimized 1000 iterations after each rotation. Also, the internal amide bond was constrained to 0° (or cis).

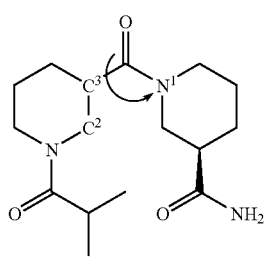

2

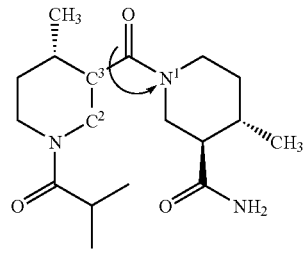

3

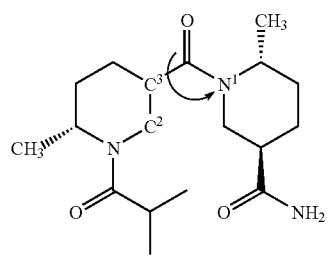

4

The relative energies were compared at each increment for all three molecules, as shown in the graphs presented in FIGS. 2A and 2B, and the preferred geometry around the C2—C3—C(O)—N1' torsion determined. The differences between molecules 2 and 4 are relatively minor; both have three minima at approximately the same energies. The lowest-energy minimum for both occurs at a C2—C3—C(O)—N1' torsion angle of 20°, and the next minimum occurs at 90° with a relative energy of +1.0 kcal/mol for 2 and +1.2 kcal/mol for 4. The final minimum is over 5.7 kcal/mol higher in energy for each molecule and occurs at 250°.

The differences between molecule 3 and the others, however, are more pronounced. First, the lowest-energy minimum occurs at a C2—C3—C(O)—N1' torsion angle of 90°; the next minimum is only 0.3 kcal/mol higher in energy and occurs at 40°. The final minimum at 250° is slightly lower in energy than for the others at +4.5 kcal/mol.

Once the conformational preferences are established, the stability of helices built from each molecule can be evaluated through dynamics simulations. First, the unsubstituted monomer, nipecotic acid, was studied. A decamer of nipecotic acid was constructed residue by residue, minimizing after each addition, thereby creating a $5_1$-helix. The resulting helix was subjected to a 200 ps molecular dynamics simulation with a timestep of 0.5 fs, again using AMBER*C and GB/SA continuous CHCl$_3$ solvation. The simulation was inconclusive.

The next helix evaluated was a decamer of TCMP. This helix was constructed by constraining the C2—C3—C(O)—N1' torsion angle to the "ideal" geometry of 90□ determined in the earlier dihedral drive simulations. The minimized conformation is a compact $3_1$-helix. A 200 ps molecular dynamics simulation was run for this decamer under the same conditions as for the nipecotic acid decamer. Unlike the previous simulation, this oligomer remained helical throughout the simulation, indicating a stable conformation. The helix also held up in a 200 ps simulation of harsher mixed-mode Monte Carlo/stoichastic dynamics. However, the most telling evidence for the stability of this helix comes from simulated annealing calculations.

The $3_1$-helix of TCMP was subjected to two simulated annealing calculations: one with a starting structure of a $3_1$-helix and one starting from a $5_1$-helix, similar to the decamer of nipecotic acid. Both simulations consisted of a 50 ps segment of molecular dynamics (1 fs timestep) at 600K to disrupt the initial conformation and a cooling phase of 400 ps in which the temperature slowly dropped from 600K to 50K. Once again, the AMBER*C force field and GB/SA continuous $CHCl_3$ solvation were used. The methyl substituent was constrained to 70°±20° with a force constant of 1000 kJ/mol (239 kcal/mol) to prevent the ring from sticking in an unproductive diaxial conformation during the cooling phase, which is a known problem with simulated annealing on six-membered rings. The final conformation from both simulations was mostly $3_1$-helical. Neither structure is a perfect helix though; both contain a ring that is in a twist-boat conformation, introducing aberrations in the helix. These results indicate that an oligomer of TCMP will form a stable helical structure.

Similar results are found for modelling studies of oligomers of trans-5-carboxy-2-methylpiperidine.

Combinatorial Chemistry:

The defined conformation conferred by the preferred polypeptides described herein makes these polyamide compounds highly useful for constructing large libraries of potentially useful compounds via combinatorial chemistry. Combinatorial exploration of functionalized oligomers of the subject compounds has a potential yield of literally millions of novel polypeptide molecules, all of which display a well-defined secondary structure.

The amino acids which comprise the finished peptides can be functionalized prior to being incorporated into a polypeptide, or unfunctionalized polypeptides can be constructed and then the entire oligomer functionalized. Neither method is preferred over the other as they are complementary depending upon the types of compounds which are desired.

Combinatorial libraries utilizing the present compounds may be constructed using any means now known to the art or developed in the future. The preferred methods, however, are the "split and pool" method using solid-phase polypeptide synthesis on inert solid substrates and parallel synthesis, also referred to as multipin synthesis.

The "split and pool" concept is based on the fact that combinatorial bead libraries contain single beads which display only one type of compound, although there may be up to $10^{13}$ copies of the same compound on a single 100 μm diameter bead. The process proceeds as follows, utilizing standard solid-phase peptide synthesis protocols as described above:

Several suitable solid substrates are available commercially. The substrates are generally small diameter beads, e.g. about 100 μm, formed from inert polymeric materials such as polyoxyethylene-grafted polystyrene or polydimethylacrylamide. An illustrative substrate, marketed under the trademark "ARGOGEL" is available from Argonaut Technologies, Washington, D.C.

Figure 10:
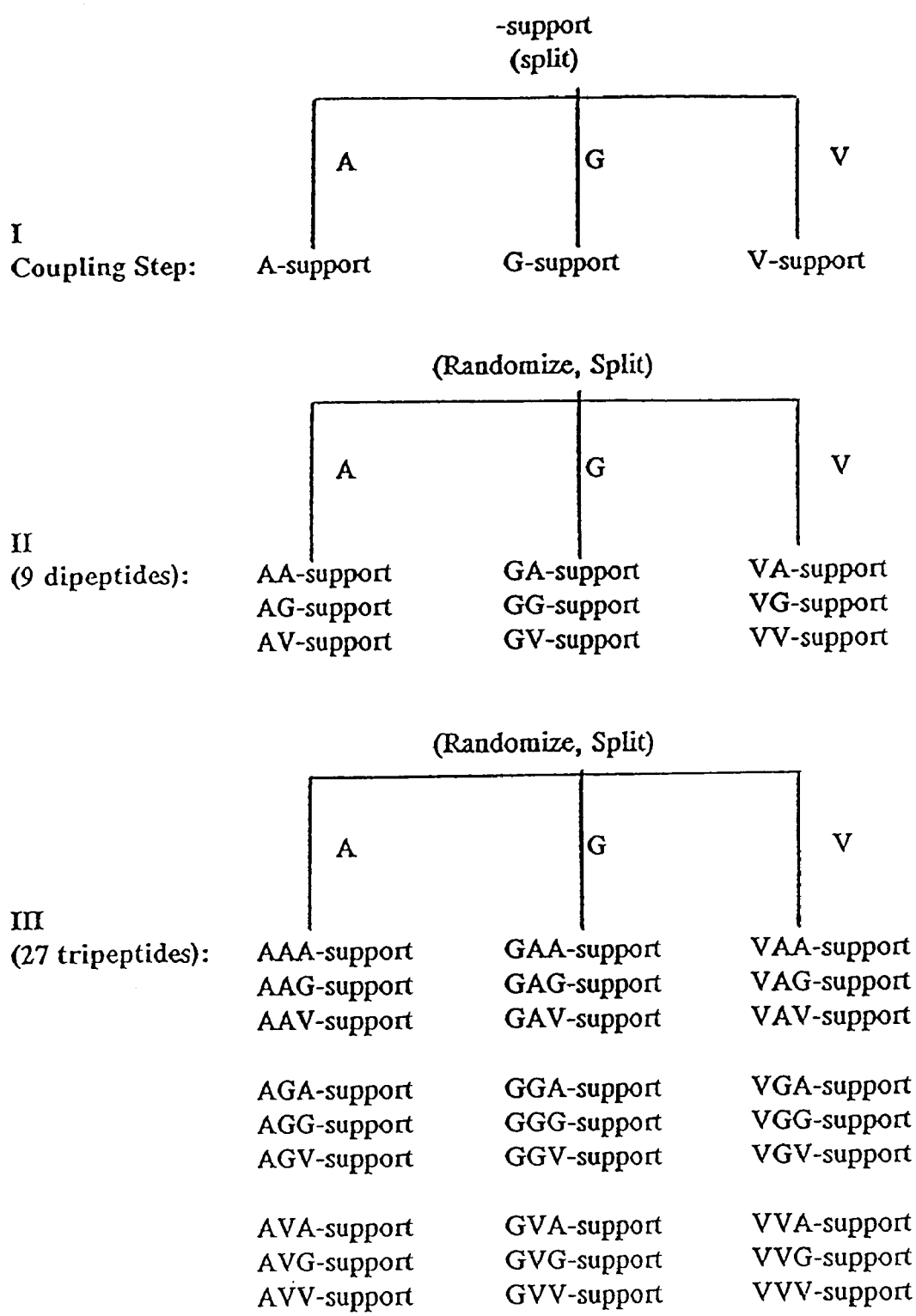
FIG. 10 is a schematic of the "split-pool" method of combinatorial chemistry.

Referring now to FIG. 10, which is a schematic depicting the split and pool method, a plurality of inert substrates are divided into two or more groups and then a first set of subunits is covalently linked to the inert support. As depicted in FIG. 10, the initial plurality of substrates is divided into three subgroups. The appearance of the three groups of beads after the first round of coupling is shown at I of FIG. 10. The three groups of beads are then pooled together to randomize the beads. The beads are then again split into a number of subgroups. Another round of coupling then takes place wherein a second subunit is bonded to the first subunit already present on each bead. The process is then repeated (theoretically ad infinitum) until the desired chain length is attained.

The split and pool process is highly flexible and has the capability of generating literally millions of different compounds which, in certain applications, can be assayed for activity while still attached to the inert substrate.

A critical aspect of the split and pool methodology is that each reaction be driven to completion prior to initiating a subsequent round of coupling. So long as each coupling reaction is driven to completion, each substrate bead will only display a single compound. Because the rate of reaction will differ from bead to bead as the library construction progresses, the beads can be monitored using conventional dyes to ensure that coupling is completed prior to initiating another round of synthesis. The presence of only a single compound per bead comes about because each individual bead encounters only one amino acid at each coupling cycle. So long as the coupling cycle is driven to completion, all available coupling sites on each bead will be reacted during each cycle and therefore only one type of peptide will be displayed on each bead.

The resulting combinatorial library is comprised of a plurality of inert substrates, each having covalently linked thereto a different polypeptide. The polypeptides can be screened for activity while still attached to the inert support, if so desired and feasible for the activity being investigated. Beads which display the desired activity are then isolated and the polypeptide contained thereon characterized, e.g., by mass spectrometry. Where a solution-phase assay is to be used to screen the library, the polypeptides are cleaved from the solid substrate and tested in solution.

As applied in the present invention, one or more of the subunits coupled to the inert substrate are selected from the cyclic imino acids described herein. In this fashion, large libraries of polypeptides can be assembled.

An alternative approach to generating combinatorial libraries uses parallel synthesis. In this approach, a known set of first subunits is covalently linked to a known location on a inert substrate, one subunit type to each location. The substrate may be a series of spots on a suitable divisible substrate such as filter paper or cotton. A substrate commonly used is an array of pins, each pin being manufactured from a suitable resin, described above.

After the initial round of coupling, each pin of the array bears a first subunit covalently linked thereto. The array is then reacted with a known set of second subunits, generally different from the first, followed by reactions with a third set of subunits, and so on. During each reiteration, each individual pin (or location) is coupled with a incoming subunit selected from a distinct set of subunits, with the order of the subunits being recorded at each step. The final result is an array of polypeptides, with a different polypeptide bonded to each solid substrate. Because the ordering of the subunits is recorded, the identity of the primary sequence of the polypeptide at any given location on the substrate (i.e., any given pin) is known. As in the split and pool method, each coupling reaction must be driven to completion in order to ensure that each location on the substrate contains only a single type of polypeptide.

Large Molecule Interactions:

A use for the present compounds is as molecular probes to investigate the interactions between biological macromolecules to identify antagonists, agonists, and inhibitors of selected biological reactions. As noted above, many biological reactions take place between very large macromolecules.

The surface areas in which these reactions take place are thought by many to be far too large to be disrupted, altered, or mimicked by a small molecule. It has been difficult, if not impossible, to manufacture molecular probes of modest size that display a well-defined conformation. Because the compounds described herein assume a highly predictable helical or sheet conformation, even when functionalized, they find use as reagents to probe the interaction between large biomolecules. In addition, these molecules can serve as antagonists or agonists in biologically-important protein interaction systems.

Employing the combinatorial methods described herein greatly expands the medicinal application of the compounds as vast libraries of compounds can be screened for specific activities, such as inhibitory and antagonist activity in a selected biological reaction.

Utility:

The compounds and combinatorial libraries described herein are useful in several highly practical endeavors. For example, because the compounds adopt stable conformations and can be fabricated using combinatorial methods, they are excellent compounds to model the behavior of corresponding, naturally-occurring alpha-polypeptides. As noted above, because the beta linkages of the present compounds are not found in nature, the compounds are also useful in in vivo modelling because the compounds are not as susceptible to enzymatic degradation.

The combinatorial libraries described herein are highly useful in the screening of other compounds for desirable chemical interactions. For example, many companies market combinatorial libraries specifically for the screening of other compounds. For example, Nanosyn Combinatorial Synthesis, Inc., of Mountainview, Calif., sells a wide variety of different chemical libraries for use in screening of other compounds.

What is claimed is:

1. A compound comprising formula:

X—{A}$_n$—Y wherein n is an integer greater than 1; and
each A, independent of every other A, is selected from the group consisting of:

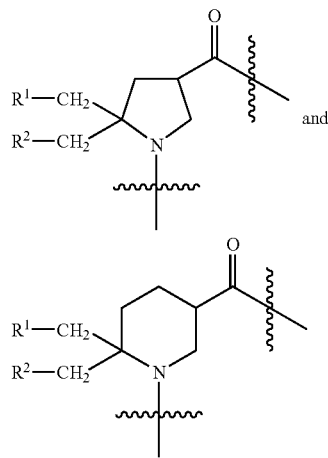

wherein $R^1$ and $R^2$ are independently selected from the group consisting of hydrogen, hydroxy, linear or branched $C_1$-$C_{16}$-alkyl, alkenyl, or alkynyl; mono-or di-$C_1$-$C_{16}$ alkylamino; mono- or bicyclic aryl; mono- or bicyclic heteroaryl having up to 5 heteroatoms selected from N, O, and S; mono- or bicyclic aryl-$C_1$-$C_{16}$-alkyl; mono- or bicyclic heteroaryl-$C_1$-$C_{16}$-alkyl; —(CH$_2$)$_{0-6}$—OR$^3$, —(CH$_2$)$_{0-6}$—SR$^3$, —(CH$_2$)$_{0-6}$—S(=O)—CH$_2$—R$^3$, —(CH$_2$)$_{0-6}$—S(=O)$_2$—CH$_2$—R$^3$, —(CH$_2$)$_{0-6}$—NR$^3$R$^3$, —(CH$_2$)$_{0-6}$—NHC(=O)R$^3$, —(CH$_2$)$_{0-6}$—NHS(=O)$_2$—CH$_2$—R$^3$, —(CH$_2$)$_{0-6}$—O—(CH$_2$)$_{2-6}$—R$^4$, —(CH$_2$)$_{0-6}$—S—(CH$_2$)$_{2-6}$—R$^4$, —(CH$_2$)$_{0-6}$—S(=O)—(CH$_2$)$_{2-6}$—R$^4$, —(CH$_2$)$_{0-6}$—S(=O)$_2$—(CH$_2$)$_{2-6}$—R$^4$, —(CH$_2$)$_{0-6}$—NH—(CH$_2$)$_{2-6}$—R$^4$, —(CH$_2$)$_{0-6}$—N—{(CH$_2$)$_{2-6}$—R$^4$}$_2$, —(CH$_2$)$_{0-6}$—NHC(=O)—(CH$_2$)$_{2-6}$—R$^4$, and —(CH$_2$)$_{0-6}$—NHS(=O)$_2$—(CH$_2$)$_{2-6}$—R$^4$; wherein $R^3$ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and $R^4$ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the substituent(s) is selected from the group consisting of $C_1$-$C_6$-alkyl, aryl, heteroaryl; O-alkylurethane, O-arylurethane, and O-heteroarylurethane;

one of X or Y is hydrogen or an amino-terminal protecting group;

the other of X or Y is hydroxy or a carboxy-terminal protecting group;

and salts thereof.

2. A compound of claim 1, wherein each A, independent of every other A, is selected from the group consisting of

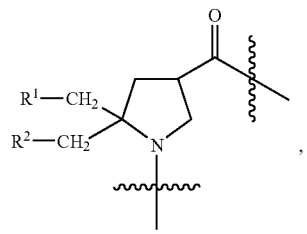

and
X, Y, $R^1$, $R^2$, and n are as defined in claim 1.

3. A compound of claim 1, wherein each A, independent of every other A, is selected from the group consisting of

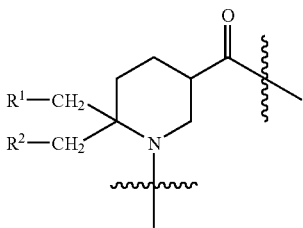

and

X, Y, R¹, R², and n are as defined in claim 1.

4. A compound comprising formula:

X—{A}$_n$—Y wherein n is an integer greater than 1; and each A, independent of every other A, is selected from the group consisting of:

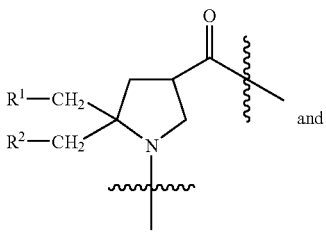

and

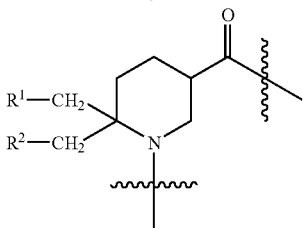

wherein R¹ and R² are independently selected from the group consisting of hydrogen, hydroxy, linear or branched $C_1$-$C_{16}$-alkyl, alkenyl, or alkynyl; mono-or di-$C_1$-$C_{16}$ alkylamino; mono- or bicyclic aryl; mono- or bicyclic heteroaryl having up to 5 heteroatoms selected from N, O, and S; mono- or bicyclic aryl-$C_1$-$C_{16}$-alkyl; mono- or bicyclic heteroaryl-$C_1$-$C_{16}$-alkyl; —(CH$_2$)$_{0-6}$—OR³, —(CH$_2$)$_{0-6}$—SR³, —(CH$_2$)$_{0-6}$—S(=O)—CH$_2$—R³, —(CH$_2$)$_{0-6}$—S(=O)$_2$—CH$_2$—R³, —(CH$_2$)$_{0-6}$—NR³R³, —(CH$_2$)$_{0-6}$—NHC(=O)R³, —(CH$_2$)$_{0-6}$—NHS(=O)$_2$—CH$_2$—R³, —(CH$_2$)$_{0-6}$—O—(CH$_2$)$_{2-6}$—R⁴, —(CH$_2$)$_{0-6}$—S—(CH$_2$)$_{2-6}$—R⁴, —(CH$_2$)$_{0-6}$—S(=O)—(CH$_2$)$_{2-6}$—R⁴, —(CH$_2$)$_{0-6}$—S(=O)$_2$—(CH$_2$)$_{2-6}$—R⁴, —(CH$_2$)$_{0-6}$—NH—(CH$_2$)$_{2-6}$R⁴, —(CH$_2$)$_{0-6}$—N—{(CH$_2$)$_{2-6}$—R⁴}$_2$, —(CH$_2$)$_{0-6}$—NHC(=O)—(CH$_2$)$_{2-6}$—R⁴, and —(CH$_2$)$_{0-6}$—NHS(=O)$_2$—(CH$_2$)$_{2-6}$—R⁴; wherein R³ is independently selected from the group consisting of hydrogen, $C_1$-$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl; and R⁴ is selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the substitutent(s) is selected from the group consisting of $C_1$-$C_6$-alkyl, aryl, heteroaryl; O-alkylurethane, O-arylurethane, and O-heteroarylurethane;

wherein one of X or Y is hydrogen or an amino-terminal protecting group selected from the group consisting of formyl, acetyl, tBoc, and Fmoc; and the other of X or Y is hydroxy or a carboxy-terminal protecting group selected from the group consisting of NH$_2$, NH(alkyl), and N(alky)$_2$;

and salts thereof.

5. A compound comprising formula:

X—{A}$_n$—Y wherein n is an integer greater than 1; and each A, independent of every other A, is selected from the group consisting of:

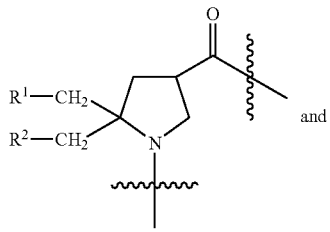

and

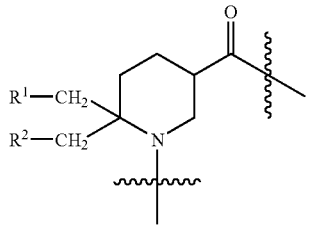

wherein R¹ and R² are independently selected from the group consisting of hydrogen, hydroxy, linear or branched $C_1$-$C_{12}$-alkyl, alkenyl, or alkynyl; mono-or di-$C_1$-$C_{12}$ alkylamino; mono- or bicyclic aryl; mono- or bicyclic heteroaryl having up to 5 heteroatoms selected from N, O, and S; mono- or bicyclic aryl-$C_1$-$C_{12}$-alkyl; and mono- or bicyclic heteroaryl-$C_1$-$C_{12}$-alkyl; and one of X or Y is hydrogen or an amino-terminal protecting group; and the other of X or Y is hydroxy or a carboxy-terminal protecting group;

and salts thereof.

6. A compound comprising formula:

X—{A}$_n$—Y wherein n is an integer greater than 1; and
each A, independent of every other A, is selected from the group consisting of:

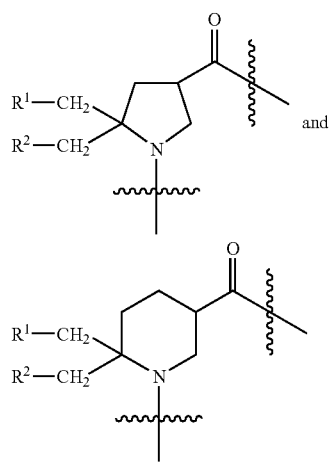

wherein R$^1$ and R$^2$ are independently selected from the group consisting of —(CH$_2$)$_{0-6}$—OR$^3$, —(CH$_2$)$_{0-6}$—SR$^3$, —(CH$_2$)$_{0-6}$—S(=O)—CH$_2$—R$^3$, —(CH$_2$)$_{0-6}$—S(=O)$_2$—CH$_2$—R$^3$, —(CH$_2$)$_{0-6}$—NR$^3$R$^3$, —(CH$_2$)$_{0-6}$—NHC(=O)R$^3$, —(CH$_2$)$_{0-6}$—NHS(=O)$_2$—CH$_2$—R$^3$, —(CH$_2$)$_{0-6}$—O—(CH$_2$)$_{2-6}$—R$^4$, —(CH$_2$)$_{0-6}$—S—(CH$_2$)$_{2-6}$—R$^4$, —(CH$_2$)$_{0-6}$—S(=O)—(CH$_2$)$_{2-6}$—R$^4$, —(CH$_2$)$_{0-6}$—S(=O)$_2$—(CH$_2$)$_{2-6}$—R$^4$, —(CH$_2$)$_{0-6}$—NH—(CH$_2$)$_{2-6}$—R$^4$, —(CH$_2$)$_{0-6}$—N{(CH$_2$)$_{2-6}$—R$^4$}$_2$, —(CH$_2$)$_{0-6}$—NHC(=O)—(CH$_2$)$_{2-6}$—R$^4$, and —(CH$_2$)$_{0-6}$—NHS(=O)$_2$—(CH$_2$)$_{2-6}$—R$^4$.; wherein R$^3$ is independently selected from the group consisting of hydrogen, C$_1$-C$_6$-alkyl, alkenyl, or alkynyl; mono- or bicyclic aryl, mono- or bicyclic heteroaryl having up to 5 heteroatoms selected from N, O, and S; mono- or bicyclic aryl-C$_1$-C$_6$-alkyl, mono- or bicyclic heteroaryl-C$_1$-C$_6$-alkyl; and R$^4$ is selected from the group consisting of hydroxy, C$_1$-C$_6$-alkyloxy, aryloxy, heteroaryloxy, thio, C$_1$-C$_6$-alkylthio, C$_1$-C$_6$-alkylsulfinyl, C$_1$-C$_6$-alkylsulfonyl, arylthio, arylsulfinyl, arylsulfonyl, heteroarylthio, heteroarylsulfinyl, heteroarylsulfonyl, amino, mono- or di-C$_1$-C$_6$-alkylamino, mono- or diarylamino, mono- or diheteroarylamino, N-alkyl-N-arylamino, N-alkyl-N-heteroarylamino, N-aryl-N-heteroarylamino, aryl-C$_1$-C$_6$-alkylamino, carboxylic acid, carboxamide, mono- or di-C$_1$-C$_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-C$_1$-C$_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the substituent(s) is selected from the group consisting of C$_1$-C$_6$-alkyl, aryl, heteroaryl; O-alkylurethane, O-arylurethane, and O-heteroarylurethane;

one of X or Y is hydrogen or an amino-terminal protecting group; and
the other of X or Y is hydroxy or a carboxy-terminal protecting group;
and salts thereof.

7. A compound of claim 6, wherein

R$^3$ is independently selected from the group consisting of hydrogen, C$_1$-C$_6$-alkyl, alkenyl, or alkynyl; mono- or bicyclic aryl, mono- or bicyclic heteroaryl having up to 5 heteroatoms selected from N, O, and S; mono- or bicyclic aryl-C$_1$-C$_6$-alkyl, mono- or bicyclic heteroaryl-C$_1$-C$_6$-alkyl; and R$^4$ is selected from the group consisting of hydroxy, C$_1$-C$_6$-alkyloxy, aryloxy, heteroaryloxy, thio, C$_1$-C$_6$-alkylthio, C$_1$-C$_6$-alkylsulfinyl, C$_1$-C$_6$-alkylsulfonyl, arylthio, arylsulfinyl, arylsulfonyl, heteroarylthio, heteroarylsulfinyl, heteroarylsulfonyl, amino, mono- or di-C$_1$-C$_6$-alkylamino, mono- or diarylamino, mono- or diheteroarylamino, N-alkyl-N-arylamino, N-alkyl-N-heteroarylamino, N-aryl-N-heteroarylamino, aryl-C$_1$-C$_6$-alkylamino, carboxylic acid, carboxamide, mono- or di-C$_1$-C$_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-C$_1$-C$_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the substituent(s) is selected from the group consisting of C$_1$-C$_6$-alkyl, aryl, heteroaryl; O-alkylurethane, O-arylurethane, and O-heteroarylurethane.

8. A compound of claim 6, wherein

R$^3$ is independently selected from the group consisting of hydrogen, C$_1$-C$_6$-alkyl, alkenyl, or alkynyl; and mono- or bicyclic aryl; and R$^4$ is selected from the group consisting of hydroxy, C$_1$-C$_6$-alkyloxy, aryloxy, heteroaryloxy, thio, C$_1$-C$_6$-alkylthio, C$_1$-C$_6$-alkylsulfinyl, C$_1$-C$_6$-alkylsulfonyl, arylthio, arylsulfinyl, arylsulfonyl, heteroarylthio, heteroarylsulfinyl, heteroarylsulfonyl, amino, mono- or di-C$_1$-C$_6$-alkylamino, mono- or diarylamino, mono- or diheteroarylamino, N-alkyl-N-arylamino, N-alkyl-N-heteroarylamino, N-aryl-N-heteroarylamino, and aryl-C$_1$-C$_6$-alkylamino.

9. A compound of claim 6, wherein

R$^3$ is selected from the group consisting of mono- or bicyclic heteroaryl having up to 5 heteroatoms selected from N, O, and S; mono- or bicyclic aryl-C$_1$-C$_6$-alkyl, and mono- or bicyclic heteroaryl-C$_1$-C$_6$-alkyl; and R$^4$ is selected from the group consisting of carboxylic acid, carboxamide, mono- or di-C$_1$-C$_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-C$_1$-C$_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the substituent(s) is selected from the group consisting of C$_1$-C$_6$-alkyl, aryl, heteroaryl; O-alkylurethane, O-arylurethane, and O-heteroarylurethane.

10. A compound comprising formula:

X—{A}$_n$—Y wherein n is an integer greater than 1; and
each A, independent of every other A, is selected from the group consisting of:

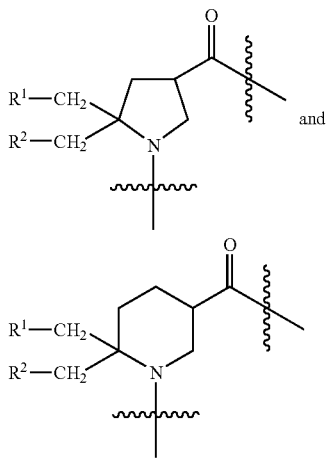

and wherein R$^1$ and R$^2$ are independently selected from the group consisting of hydrogen, hydroxy, linear or branched C$_1$-C$_6$-alkyl, alkenyl, or alkynyl; —(CH$_2$)$_{0-6}$—OR$^3$; mono-or di-C$_1$-C$_6$ alkylamino; mono- or bicyclic aryl; and mono- or bicyclic aryl-C$_1$-C$_6$-alkyl; and one of X or Y is hydrogen or an amino-terminal protecting group selected from the group consisting of formyl, acetyl, tBoc, and Fmoc; and the other of X or Y is hydroxy or a carboxy-terminal protecting group selected from the group consisting of NH$_2$, NH(alkyl), and N(alkyl)$_2$.

11. A compound of claim 1, wherein R$^1$ and R$^2$ are independently selected from the group consisting of hydrogen, hydroxy, linear or branched C$_1$-C$_6$-alkyl, monocyclic aryl, and monocyclic aryl-C$_1$-C$_6$-alkyl.

12. A combinatorial array comprising a plurality of distinct oligomers or polymers of compounds according to claim 1 at selected, known locations on a substrate or in discrete solutions, wherein each of the oligomers or polymers of claim 1 is substantially pure within each of the selected known locations or discrete solutions and has a composition that is different from other oligomers or polymers disposed at other selected and known locations on the substrate or in other discrete solutions.

13. A compound of claim 5, wherein one of X or Y is hydrogen or an amino-terminal protecting group selected from the group consisting of formyl, acetyl, tBoc, and Fmoc; and the other of X or Y is hydroxy or a carboxy-terminal protecting group selected from the group consisting of NH$_2$, NH(alkyl), and N(alkyl)$_2$.

14. A compound of claim 6, wherein one of X or Y is hydrogen or an amino-terminal protecting group selected from the group consisting of formyl, acetyl, tBoc, and Fmoc; and the other of X or Y is hydroxy or a carboxy-terminal protecting group selected from the group consisting of NH$_2$, NH(alkyl), and N(alkyl)$_2$.

15. A compound comprising formula:

X—{A}$_n$—Y wherein n is an integer greater than 1; and
each A, independent of every other A, is selected from the group consisting of:

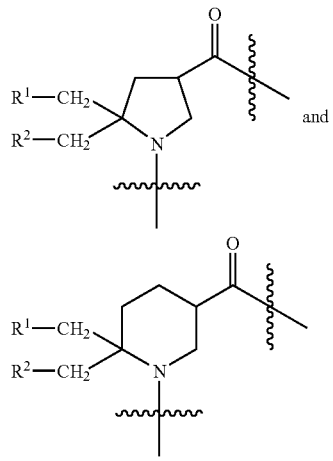

and wherein R$^1$ and R$^2$ are independently selected from the group consisting of hydrogen, hydroxy, linear or branched C$_1$-C$_6$-alkyl, monocyclic aryl, and monocyclic aryl-C$_1$-C$_6$-alkyl; and one of X or Y is hydrogen or an amino-terminal protecting group selected from the group consisting of formyl, acetyl, tBoc, and Fmoc; and the other of X or Y is hydroxy or a carboxy-terminal protecting group selected from the group consisting of NH$_2$, NH(alkyl), and N(alkyl)$_2$.

* * * * *